(12) United States Patent
Landers et al.

(10) Patent No.: US 8,753,818 B1
(45) Date of Patent: Jun. 17, 2014

(54) METHODS OF DETECTING AMYOTROPHIC LATERAL SCLEROSIS (ALS)

(71) Applicant: The University of Massachuetts, Boston, MA (US)

(72) Inventors: John E. Landers, Shrewsbury, MA (US); Robert H. Brown, Shrewsbury, MA (US)

(73) Assignee: The University of Massachusetts, Boston, MA (US)

( * ) Notice: Subject to any disclaimer, the term of this patent is extended or adjusted under 35 U.S.C. 154(b) by 0 days.

(21) Appl. No.: 13/833,898

(22) Filed: Mar. 15, 2013

Related U.S. Application Data

(60) Provisional application No. 61/729,855, filed on Nov. 26, 2012.

(51) Int. Cl.
 *C12Q 1/68* (2006.01)
(52) U.S. Cl.
 USPC .......................................... 435/6.11; 435/6.16
(58) Field of Classification Search
 None
 See application file for complete search history.

(56) References Cited

PUBLICATIONS

Al-Chalabi, A. et al., "Deletions of the Heavy Neurofilament Subunit Tail in Amyotrophic Lateral Sclerosis", *Human Molecular Genetics*, 8(2): 157-164 (1999).
Bosco, D.A., et al., "Wild-Type and Mutant SOD1 Share an Aberrant Conformation and a Common Pathogenic Pathway in ALS", *Nature Neuroscience*, 13(11): 1396-1403 (2010).
Braun, A., et al., "Genomic Organization of Profilin-III and Evidence for a Transcript Expressed Exclusively in Testis", *Gene*, 283: 219-225 (2002).
Deng, H-X., et al., "Mutations in UBQLN2 Cause Dominant X-Linked Juvenile and Adult Onset ALS and ALS/Dementia", *Nature*, 477: 211-215 (2011).
DeJesus-Hernandez, M., et al., "Expanded GGGGCC Hexanucleotide Repeat in Noncoding Region of C9ORF72 Causes Chromosome 9p-Linked FTD and ALS", *Neuron*, 72: 245-256 (2011).
Duan, W., et al., "MG132 Enhances Neurite Outgrowth in Neurons Overespressing Mutant TAR DNA-Binding Protein-43 Via Increase OF HO-1", *Brain Research*, 1397: 1-9 (2011).
Fujii, R., et al., "The RNA Binding Protein TLS is Translocated to Dendritic Spines by mGluR5 Activation and Regulates and Regulates Spine Morphology", *Current Biology*, 15: 587-593 (2005).
Giesemann, T., et al., "A Role for Polyproline Motifs in the Spinal Muscular Atrophy Protein SMN", *Journal of Biological Chemistry*, 274(53): 37908-37914 (1999).
Gijselinck, I., et al., "A C9orf72 Promotor Repeat Expansion in a Flanders-Belgian Cohort with Disorders of the Frontotemporal Lobar Degeneration-Amyotrophic Lateral Sclerosis Spectrym: A Gene Identififcation Study", *Lancet Neurology*, 11: 54-65 (2012).
Gros-Louis, F., et al., "A Frameshift Deletion in Peripherin Gene Associate With Amyotrophic Lateral Sclerosis", *Journal of Biology Chemistry*, 279(44): 45951-45956 (2004).
Hazan, J., et al., "Spastin, A New AAA Protein, is Altered in the Most Frequent Form of Autosomal Deminant Spastic Paralegia", *Nature Genetics*, 3: 296-303 (1999).
Johnson, J.O., et al., "Exome Sequensing Reveals VCP Mutations as a Cause of Familial ALS", *Neuron*, 68: 857-864 (2010).
KAbashi, E., et al., "TARDBP Mutations in Individuals With Sporadic and Familial Amyotrophic Lateral Scleroso", *Nature Genetics*, 40(5): 572-574 (2008).
Kwiatkowski, Jr., T.J., et al., "Mutations in the FUS/TLS Gene on Chromosome 16 Cause Familial Amyotrophic Lateral Sclerosis", *Science*, 323: 1205-1208 (2009).
Landers, J.E., et al., "Reduced Expression of the Kinesin-Associated Protein 3 (KIFAP3) Gene Increases Survival in Sporadic Amyotrophic Lateral Sclerosis", *PNAS*, 106(22): 9004-9009 (2009).
Meijering, E., et al. "Design and Validation of a Tool for Neurite Tracing and Analysis in Fluorescence Microscopy Images", *Cytometry Part A*, 58A:167-176 (2004).
Mersiyanova, I.V., et al., "A New Variant of Charcot-Marie-Tooth Disease Type 2 Is Probably the Result of a Mutation in the Neurofilament-Light Gene", *Am J. Hum. Genet.*, 67: 37-46 (2000).
Mockrin, S.C. and Korn, E.D., "Acanthamoeba Profilin Interacts With G-Actin to Increase the Rate of Exchange of Actin-Bound Adenosine 5'-Triphophate", *Biochemistry*, 19(23): 5359-5362 (1980).
Perrot, R. And Eyer, J. "Neuronal Intermediate Filaments and Neurodegenerative Disorders", *Brain Res. Bull.*, 80: 282-295 (2009).
Puls, I., et al., "Mutant Dynactin in Motor Neuron Disease", *Nature Genetics* 33: 455-456 (2003).
Reid, E., et al.,"A Kinesin Heavy Chain (KIF5A) Mutation in Hereditary Spastic Paraplegia (SPG10)", *Am. J. Hum. Genet.*, 71: 1189-1194 (2002).
Renton, A.E., et al., "A Hexanucleotide Repeat Expansion in C9ORF72 Is the Cause of Chromosome 9p21-Linked ALS-FTD", *Neuron*, 72: 257-268 (2011).
Schutt, C.E., et al., "The Structure of Crystalline Profilin-β-Actin", *Nature*, 365: 810-816 (1993).

(Continued)

*Primary Examiner* — John Ulm
(74) *Attorney, Agent, or Firm* — Hamilton, Brook, Smith & Reynolds, P.C.

(57) ABSTRACT

In one aspect, the invention is directed to a method of identifying an individual that has amyotrophic lateral sclerosis (ALS) or is at risk of developing ALS comprising detecting one or more alterations in a profilin 1 (PFN1) sequence of an individual in need thereof compared to a wild type profilin sequence. In another aspect, the invention is directed to a method of identifying an individual that has amyotrophic lateral sclerosis (ALS) or is at risk of developing ALS comprising selectively sequencing a profilin 1 (PFN1) sequence of an individual in need thereof; and detecting one or more alterations in the PFN1 sequence of the individual. If the one or more alterations are detected then the individual has ALS.

14 Claims, 18 Drawing Sheets

(56) References Cited

PUBLICATIONS

Shao, J., et al., "Phophorylation of Profilin by ROCK1 Regulates Polyglutamine Aggregation", *Mol. Cell. Biol.*, 28(17): 5196-5208 (2008).

Sreedharan, J., et al., "TDP-43 Mutations in Familial and Sporadic Amyotrophic Lateral Sclerosis", *Science*, 319: 1668-1672 (2008).

Suetsugu, S., et al., "The Essential Role of Profilin in the Assembly of Actin for Microspike Formation", *The EMBO Journal*, 17(22): 6516-6526 (1998).

Takeuchi, H., et al., "Hsp70 and Hsp40 Improve Neurite Outgrowth and Suppress Intracytoplasmic Aggregate Formation in Cultured Neuronal Cells Expressing Mutant SOD1", *Brain Research*, 949: 11-22 (2002).

Tilney, L.G., et al., "Actin From *Thyone* Sperm Assembles on Only One End of an Actin Filament: A Behavior Regulated by Profilin", *The Journal of Cell Biology*, 97: 112-124 (1983).

Vance, C., et al., "Mutations in FUS, An RNA Processing Protein, Cause Familial Amyotrophic Lateral Sclerosis Type 6", *Science*, 323: 1208-1211 (2009).

Wills, Z., et al., "Profilin and the Abl Tyrosine Kinase Are Required for Motor Axon Outgrowth in the *Drosophia* Embryo", *Neuron*, 22: 291-299 (1999).

Witke, W., et al., "In Mouse Brain Profilin I and Profilin II Associate With Regulators of the Endocytic Pathyway and Actin Assembly", *The EMBO Journal*, 17(4): 967-976 (1998).

Witke, W., "The Role of Profilin Complexes in Cell Motility and Other Cellular Processes", *Trends Cell Biol.*, 14(8): 461-469 (2004).

Wu, C.-H., et al., "Mutations in the Profilin 1 Gene Cause Familial Amyotrophic Lateral Sclerosis", *Nature*, 488: 499-503 (2012).

Figure 20

>uc002gaa.3 PFN1 amino acid sequnece length=140

MAGWNAYIDNLMADGTCQDAAIVGYKDSPSVWAAVPGKTFVNITPAEVGVLVGKDRSSFY
VNGLTLGGQKCSVIRDSLLQDGEFSMDLRTKSTGGAPTFNVTVTKTDKTLVLLMGKEGVH
GGLINKKCYEMASHLRRSQY (SEQ ID NO: 2)

>uc002gaa.3 PFN1 nucleotide sequence length=847 acagcgagcggagccgcggtccggacggcagcgcgtgccccgagctctccgcctcccccgcccgccagccgaggcagctcgagcc
cagtccgcggcccccagcagcagcgccgagagcagccccagtagcagcgccatggccgggtggaacgcctacatcgacaacctcatgg
cggacgggacctgtcaggacgcggccatcgtgggctacaaggactcgccctccgtctgggccgccgtccccgggaaaacgttcgtcaac
atcacgccagctgaggtgggtgtcctggttggcaaagaccggtcaagttttacgtgaatgggctgacacttgggggccagaaatgttcggt
gatccgggactcactgctgcaggatgggggaatttagcatggatcttcgtaccaagagcaccggtggggccccacctttcaatgtcactgtca
ccaagactgacaagacgctagtcctgctgatgggcaaagaaggtgtccacggtggtttgatcaacaagaaatgttatgaaatggcctccca
ccttcggcgttcccagtactgacctcgtctgtcccttcccttcaccgctccccacagctttgcacccctttcctccccatacacacacaaacca
tttattttttgggccattaccccataccccttattgctgccaaaaccacatgggctgggggccagggctggatggacagacacctcccectac
ccatatccctcccgtgtgtggttggaaaactttgttttttggggttttttttttctgaataaaaaagattctactaacaaaaaaaaaaaaaaaaaa
aaaaaaaaaaaaaaaaaaaaaa (SEQ ID NO: 1)

SEQUENCE LISTING

```
<160> NUMBER OF SEQ ID NOS: 8

<210> SEQ ID NO 1
<211> LENGTH: 847
<212> TYPE: DNA
<213> ORGANISM: unknown
<220> FEATURE:
<223> OTHER INFORMATION: PFN1 nucleotide squence

<400> SEQUENCE: 1
acagcgagcg gagccgcggt ccggacggca gcgcgtgccc cgagctctcc gcctccccc       60 gcccgccagc cgaggcagct cgagcccagt ccgcggcccc agcagcagcg ccgagagcag     120
ccccagtagc agcgccatgg ccgggtggaa cgcctacatc gacaacctca tggcggacgg     180
```

```
gacctgtcag gacgcggcca tcgtgggcta caaggactcg ccctccgtct gggccgccgt    240
ccccgggaaa acgttcgtca acatcacgcc agctgaggtg ggtgtcctgg ttggcaaaga    300
ccggtcaagt ttttacgtga atgggctgac acttggggc cagaaatgtt cgtgatccg     360 ggactcactg ctgcaggatg gggaatttag catggatctt cgtaccaaga gcaccggtgg    420
ggcccccacc ttcaatgtca ctgtcaccaa gactgacaag acgctagtcc tgctgatggg    480
caaagaaggt gtccacggtg gtttgatcaa caagaaatgt tatgaaatgg cctcccacct    540
tcggcgttcc cagtactgac ctcgtctgtc ccttccccct caccgctccc cacagctttg    600 caccccttc ctccccatac acacacaaac cattttattt tttgggccat taccccatac    660
cccttattgc tgccaaaacc acatgggctg ggggccaggg ctggatggac agacacctcc    720
ccctacccat atccctcccg tgtgtggttg gaaaactttt gttttttggg gttttttttt    780
tctgaataaa aagattcta ctaacaaaaa aaaaaaaaaa aaaaaaaaaa aaaaaaaaa     840 aaaaaaa                                                             847
```

<210> SEQ ID NO 2
<211> LENGTH: 140
<212> TYPE: PRT
<213> ORGANISM: unknown
<220> FEATURE:
<223> OTHER INFORMATION: PFN1 amino acid squence

<400> SEQUENCE: 2

```
Met Ala Gly Trp Asn Ala Tyr Ile Asp Asn Leu Met Ala Asp Gly Thr
 1               5                  10                  15

Cys Gln Asp Ala Ala Ile Val Gly Tyr Lys Asp Ser Pro Ser Val Trp
            20                  25                  30

Ala Ala Val Pro Gly Lys Thr Phe Val Asn Ile Thr Pro Ala Glu Val
        35                  40                  45

Gly Val Leu Val Gly Lys Asp Arg Ser Ser Phe Tyr Val Asn Gly Leu
    50                  55                  60

Thr Leu Gly Gly Gln Lys Cys Ser Val Ile Arg Asp Ser Leu Leu Gln
65                  70                  75                  80

Asp Gly Glu Phe Ser Met Asp Leu Arg Thr Lys Ser Thr Gly Gly Ala
                85                  90                  95

Pro Thr Phe Asn Val Thr Val Thr Lys Thr Asp Lys Thr Leu Val Leu
            100                 105                 110

Leu Met Gly Lys Glu Gly Val His Gly Gly Leu Ile Asn Lys Lys Cys
        115                 120                 125

Tyr Glu Met Ala Ser His Leu Arg Arg Ser Gln Tyr
    130                 135                 140
```

<210> SEQ ID NO 3
<211> LENGTH: 11
<212> TYPE: PRT
<213> ORGANISM: unknown
<220> FEATURE:
<223> OTHER INFORMATION: human PFN1 C71G mutation

<400> SEQUENCE: 3

```
Leu Gly Gly Gln Lys Cys Ser Val Ile Arg Asp
 1               5                  10
```

<210> SEQ ID NO 4
<211> LENGTH: 15
<212> TYPE: PRT
<213> ORGANISM: unknown

```
<220> FEATURE:
<223> OTHER INFORMATION: human PFN1 M114T, E117G, G118V mutation

<400> SEQUENCE: 4

Thr Leu Val Leu Leu Met Gly Lys Glu Gly Val His Gly Gly Leu
 1               5                  10                  15

<210> SEQ ID NO 5
<211> LENGTH: 15
<212> TYPE: PRT
<213> ORGANISM: unknown
<220> FEATURE:
<223> OTHER INFORMATION: cow PFN1 M114T, E117G, G118V mutation

<400> SEQUENCE: 5

Thr Leu Val Leu Leu Met Gly Lys Glu Gly Val His Gly Gly Met
 1               5                  10                  15

<210> SEQ ID NO 6
<211> LENGTH: 12
<212> TYPE: PRT
<213> ORGANISM: unknown
<220> FEATURE:
<223> OTHER INFORMATION: armadillo PFN1 M114T, E117G, G118V mutation

<400> SEQUENCE: 6

Gln Leu Met Gly Lys Glu Gly Val His Ser Ser Leu
 1               5                  10

<210> SEQ ID NO 7
<211> LENGTH: 11
<212> TYPE: PRT
<213> ORGANISM: unknown
<220> FEATURE:
<223> OTHER INFORMATION: zebrafish PFN1 C17G mutation

<400> SEQUENCE: 7

Leu Gly Lys Lys Lys Cys Ser Val Ile Arg Asp
 1               5                  10

<210> SEQ ID NO 8
<211> LENGTH: 15
<212> TYPE: PRT
<213> ORGANISM: unknown
<220> FEATURE:
<223> OTHER INFORMATION: zebrafish PFN1 M114T, E117G, G118V mutation

<400> SEQUENCE: 8

Val Leu Val Leu Leu Met Gly Lys Glu Gly Val His Gly Gly Gly
 1               5                  10                  15
```

METHODS OF DETECTING AMYOTROPHIC LATERAL SCLEROSIS (ALS)

RELATED APPLICATION

This application claims the benefit of U.S. Provisional Application No. 61/729,855, filed on Nov. 26, 2012. The entire teachings of the above application are incorporated herein by reference.

GOVERNMENT SUPPORT

This invention was made with government support under grant nos. NS073873, NS050557 and NS070342 from the National Institutes of Health. The government has certain rights in the invention.

INCORPORATION BY REFERENCE OF MATERIAL IN ASCII TEXT FILE

This application incorporates by reference the Sequence Listing contained in the following ASCII text file:
a) File name: 07462005001SEQLIST.txt; created Sep. 17, 2013, 4 KB in size.

BACKGROUND OF THE INVENTION

Amyotrophic lateral sclerosis (ALS) is a late-onset neurodegenerative disorder resulting from motor neuron death. Approximately 10% of cases are familial (FALS), typically with a dominant inheritance mode. Despite numerous advances in recent years (Kabashi, E. et al. Nature Genet. 40, 572-574 (2008); Sreedharan, J. et al. Science 319, 1668-1672 (2008); Kwiatkowski, T. J. Jr et al. Science 323, 1205-1208 (2009); Vance, C. et al. Science 323, 1208-1211 (2009); Johnson, J. O. et al. Neuron 68, 857-864 (2010); DeJesus-Hernandez, M. et al. Neuron 72, 245-256 (2011); Deng, H. X. et al. Nature 477, 211-215 (2011); Renton, A. E. et al. Neuron 72, 257-268 (2011); Gijselinck, I. et al. Lancet Neurol. 11, 54-65 (2012)), nearly 50% of FALS cases have unknown genetic aetiology.

A need exists for methods of detecting and treating ALS and FALS.

SUMMARY OF THE INVENTION

In one aspect, the invention is directed to a method of identifying an individual that has amyotrophic lateral sclerosis (ALS), or is at risk of developing ALS, comprising detecting one or more alterations in a profilin 1 (PFN1) sequence of an individual in need thereof compared to a wild type profilin sequence.

In another aspect, the invention is directed to a method of identifying an individual that has amyotrophic lateral sclerosis (ALS), or is at risk of developing ALS, comprising selectively sequencing a profilin 1 (PFN1) sequence in a sample of an individual in need thereof; and detecting one or more alterations in the PFN1 sequence of the individual compared to the wild type PFN1 sequence. If the one or more alterations are detected then the individual has ALS.

In particular aspects, the one or more alterations results in the PFN1 sequence encoding a PFN1 protein sequence having a C71G alteration, a M114T alteration, a G118V alteration, an E117G alteration or a combination thereof. In other aspects, the ALS is FALS.

BRIEF DESCRIPTION OF THE DRAWINGS

FIG. 20: The nucleotide sequence (SEQ ID NO: 1) and the amino acid sequence (SEQ ID NO: 2) of wild type human PFN1.

DETAILED DESCRIPTION OF THE INVENTION

Figures 1A, 1B, 1C, 1D:
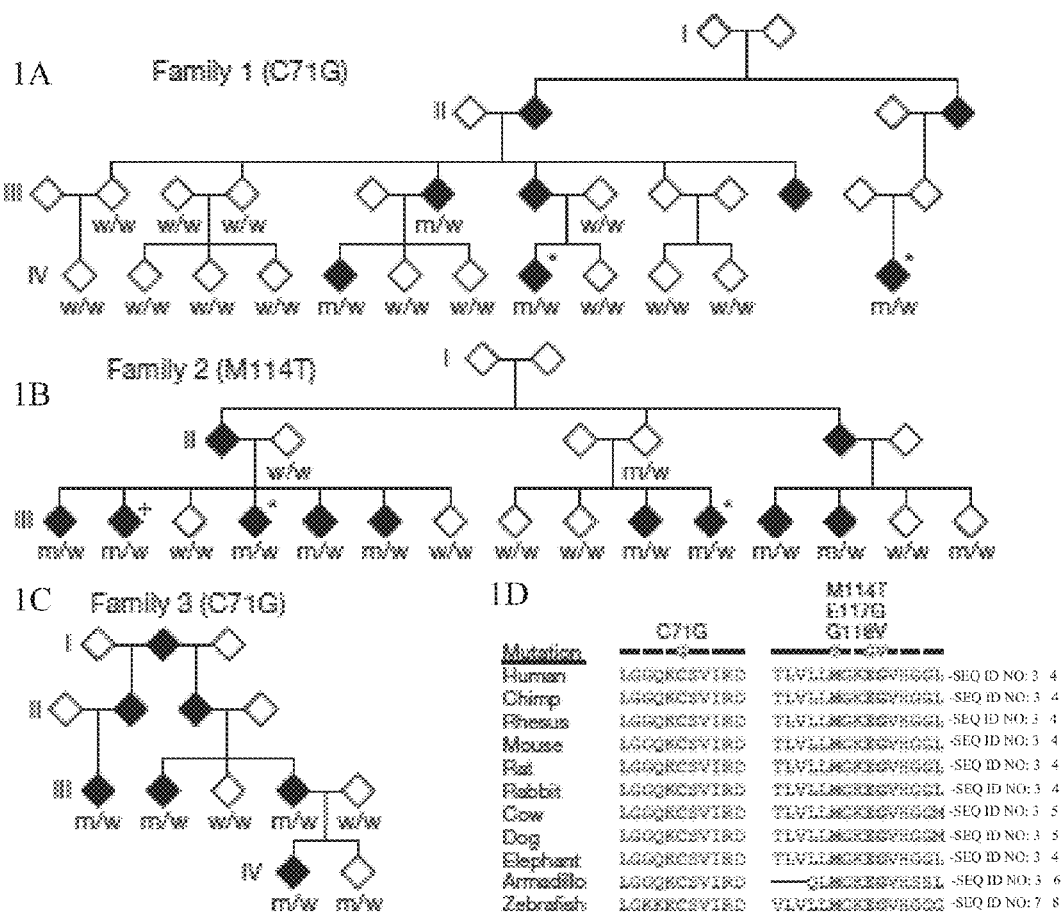
FIGS. 1A-1D: Exome sequencing identifies PFN1 gene mutations in familial ALS. 1A-1C: Familial ALS pedigrees containing PFN1 mutations are shown. Asterisks indicate samples subjected to exome sequencing. To prevent identification of individual family members, the gender of each subject and information on the lower generation were withheld. Genotypes of available DNA samples for the indicated PFN1 mutation are shown ('w' denotes wild type, 'm' denotes mutant). The genotype of sample III:2 in family 2 (1) was inferred from the genotypes of spouse and progeny (not shown). 1D: The evolutionary conservation of PFN1 mutations is shown. For each, the mutated amino acid (SEQ ID NOs: 3-8) highlighted.

Shown herein is that one or more mutations within the profilin 1 (PFN1) sequence can cause ALS such as FALS. PFN1 is crucial for the conversion of monomeric (G)-actin to filamentous (F)-actin. Exome sequencing of two large ALS families showed different mutations within the PFN1 gene. Further sequence analysis identified 4 mutations in 7 out of 274 FALS cases. Cells expressing PFN1 mutants contained ubiquitinated, insoluble aggregates that in many cases contain the ALS-associated protein TDP-43. PFN1 mutants also displayed decreased bound actin levels and inhibited axon outgrowth. Furthermore, primary motor neurons expressing mutant PFN1 displayed smaller growth cones with a reduced F/G-actin ratio. These observations further document that cytoskeletal pathway alterations contribute to ALS pathogenesis.

Accordingly, in one aspect, the invention is directed to a method of identifying an individual that has amyotrophic lateral sclerosis (ALS), or is at risk of developing ALS comprising detecting one or more alterations in a profilin 1 (PFN1) sequence of an individual in need thereof compared to a wild type profilin sequence.

In another aspect, the invention is directed to a method of identifying an individual that has amyotrophic lateral sclerosis (ALS), or is at risk of developing ALS, comprising selectively sequencing a profilin 1 (PFN1) sequence in a sample of an individual in need thereof; and detecting one or more alterations in the PFN1 gene sequence of the individual compared to the wild type PFN1 gene sequence. If the one or more alterations are detected then the individual has ALS.

As used herein amyotrophic lateral sclerosis (ALS), often referred to as Lou Gehrig's Disease, is a rapidly progressive, invariably fatal neurological disease that attacks the nerve cells (neurons) responsible for controlling voluntary muscles. The disease belongs to a group of disorders known as motor neuron diseases, which are characterized by the gradual degeneration and death of motor neurons. Motor neurons are nerve cells located in the brain, brainstem, and spinal cord that serve as controlling units and vital communication links between the nervous system and the voluntary muscles of the body. Messages from motor neurons in the brain (called upper motor neurons) are transmitted to motor neurons in the spinal cord (called lower motor neurons) and from them to particular muscles. In ALS, both the upper motor neurons and the lower motor neurons degenerate or die, ceasing to send messages to muscles. Unable to function, the muscles gradually weaken, waste away (atrophy), and twitch (fasciculations). Eventually, the ability of the brain to start and control voluntary movement is lost. All muscles under voluntary control are affected, and patients lose their strength and the ability to move their arms, legs, and body. When muscles in the diaphragm and chest wall fail, patients lose the ability to breathe without ventilatory support. Most people with ALS die from respiratory failure, usually within 3 to 5 years from the onset of symptoms. Although the disease usually does not impair a person's mind or intelligence, several recent studies suggest that some ALS patients may have alterations in cognitive functions such as depression and problems with decision-making and memory.

As many as 20,000-30,000 people in the United States have ALS, and an estimated 5,000 people in the United States are diagnosed with the disease each year. ALS is one of the most common neuromuscular diseases worldwide, and people of all races and ethnic backgrounds are affected. ALS most commonly strikes people between 40 and 60 years of age, but younger and older people also can develop the disease. Men are affected more often than women. Approximately 90 to 95 percent of all ALS cases occurs apparently at random with no clearly associated risk factors. Patients do not have a family history of the disease, and their family members are not considered to be at increased risk for developing this type of ALS, also referred to as sporadic ALS.

About 5 to 10 percent of all ALS cases are inherited. The familial form of ALS, referred to herein as familial ALS or FALS, usually results from a pattern of inheritance that requires only one parent to carry the gene responsible for the disease. About 20 percent of all familial cases result from a specific genetic defect that leads to mutation of the enzyme known as superoxide dismutase 1 (SOD1). Research on this mutation is providing clues about the possible causes of motor neuron death in ALS. Not all familial ALS cases are due to the SOD1 mutation, therefore as shown herein, other genetic causes clearly exist.

In particular aspects of the invention, the ALS is familial amyotrophic lateral sclerosis (FALS). In yet another aspect, the individual has been previously diagnosed with amyotrophic lateral sclerosis. In yet other aspects, the individual can be symptomatic or asymptomatic for ALS and/or FALS.

PFN1 refers to a 140-amino-acid protein and major growth regulator of filamentous (F)-actin through its binding of monomeric (G)-actin (Mockrin, S C & Korn E D, *Biochem,* 19:5359-5362 (1980)). PFN1 regulates actin polymerization and promotes nucleotide exchange on actin, converting monomeric ADP-actin to ATP-actin (Mockrin, S. C. & Korn, E. D. Biochemistry 19, 5359-5362 (1980). PFN1-ATP-actin complexes can bind to the fast-growing end of actin filaments. Dissociation of the complex allows the ATP-actin monomer to be added to the growing actin filament (Tilney, L. G. et al. J. Cell Biol. 97, 112-124 (1983)).

As used herein, one or more alterations in a PFN1 sequence is an alteration or variation in a PFN1 sequence from its natural (wild type) state that causes or is associated with ALS and/or FALS. In a particular aspect, the one or more alterations in the PFN1 gene disrupt one or more cytoskeletal pathways in the individual. In a particular aspect, the alteration includes one or more mutations in a PFN1 sequence. A mutation is a change in a nucleic acid (e.g., DNA) sequence compared to the wild type sequence. Mutations can result from DNA copying mistakes made during cell division, exposure to ionizing radiation, exposure to chemicals called mutagens, or infection by viruses. Germ line mutations occur in the eggs and sperm and can be passed on to offspring, while somatic mutations occur in body cells and are not passed on. Wild type (wt) PFN1 refers to the PFN1 sequence of the PFN1 sequence as it typically occurs in nature (and is not associated with ALS).

In the methods provided herein, one or more alterations in the PFN1 sequence is detected. The alteration can be detected in the nucleotide and/or amino acid sequence of PFN1. As used herein, a PFN1 nucleotide sequence includes all or a portion of a PFN1 gene sequence and/or a PFN1 coding sequence. A PFN1 gene sequence refers to all or a portion of the entire PFN1 nucleic acid sequence that is necessary for the synthesis of a functional PFN1 polypeptide (e.g., exons; introns; upstream sequences; downstream sequences). Thus, the PFN1 gene sequence can include more than the nucleotides encoding the amino acid sequence of the PFN1 protein, referred to as the PFN1 coding region. A PFN1 gene sequence can include the DNA sequences required for coding a PFN1 polypeptide (protein) or the DNA sequences required for synthesis of a PFN1 RNA transcript. Other noncoding regions in a PFN1 gene sequence include enhancer sequences and sequences that specify 3' cleavage and polyadenylation [poly(A) sites] and splicing of primary RNA transcripts. In a particular aspect, the one or more alterations in the PFN1 sequence results in a PFN1 protein having a C71G alteration, a M114T alteration, a G118V alteration, an E117G alteration or a combination thereof.

In the methods of the invention, the one or more alterations in the PFN1 sequence can be detected in a sample (biological sample) of the individual. Thus, the method can further comprise obtaining a (one or more) sample from the individual. The sample can be, for example, a biological fluid, a biological tissue (e.g., a biopsy) and combinations thereof from the individual. Examples of biological fluids include blood, plasma, lymph, cerebrospinal fluid, urine saliva, amniotic fluid and the like. Examples of biological tissues include skin, hair, bone, cells and the like. Methods for obtaining such biological samples from an individual are known to those of skill in the art.

As described herein, methods of identifying an individual that has, or is at risk of developing, ALS or FALS comprise detecting one or more alterations in a PFN1 sequence of the individual. A variety of methods for detecting an alteration in a PFN1 sequence can be used in the methods of the invention. In a particular aspect of the invention, a PFN1 sequence of the individual is selectively sequenced in order to detect one or more alterations in the PFN1 sequence.

Examples of such methods include exome sequencing, sanger gene sequencing, resequencing array analysis, mRNA analysis/cDNA sequencing polymerase chain reaction (PCR), single-strand conformation polymorphism (sscp), heteroduplex analysis (het), allele-specific oligonucleotide (aso), restriction fragment analysis, allele-specific amplification (asa), single nucleotide primer extension, oligonucleotide ligation assay (ola), denaturing gradient gel electrophoresis (DGGE), temperature gradient gel electrophoresis (TGGE), single strand conformation polymorphism (SSCP), sequencing using molecular invasion probes (MIPs) or combinations thereof. In a particular aspect, the PFN1 sequence of the individual is selectively sequenced by performing exome sequencing, e.g., on a sample of the individual.

As will be appreciated by those of skill in the art, the detection of the one or more alterations in the PFN1 sequence of the individual can be compared to a control. A variety of controls can be used. In one aspect, the control is a wild type PFN1 sequence. In another aspect, the control is a sample obtained from one or more individuals that do not have ALS or FALS. In yet another aspect, the control is a reference standard.

If one or more of the alterations in the profilin 1 (PFN1) sequence of the individual is detected using the methods described herein, the methods can further comprise treating the individual for ALS or FALS and/or the symptoms thereof. For example, the individual can be treated with a drug such as riluzole (Rilutek) which can slow the disease progression and prolong life. Treatments to control symptoms include use of drugs such as baclofen or diazepam to control spasticity, and/or trihexyphenidyl or amitriptyline address problems swallowing. Such individuals can be treated either before or after ALS or FALS manifests in the individual.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

EXEMPLIFICATION

Mutations in the Profilin 1 Gene Cause Familial Amyotrophic Lateral Sclerosis

Figures 5A, 5B:
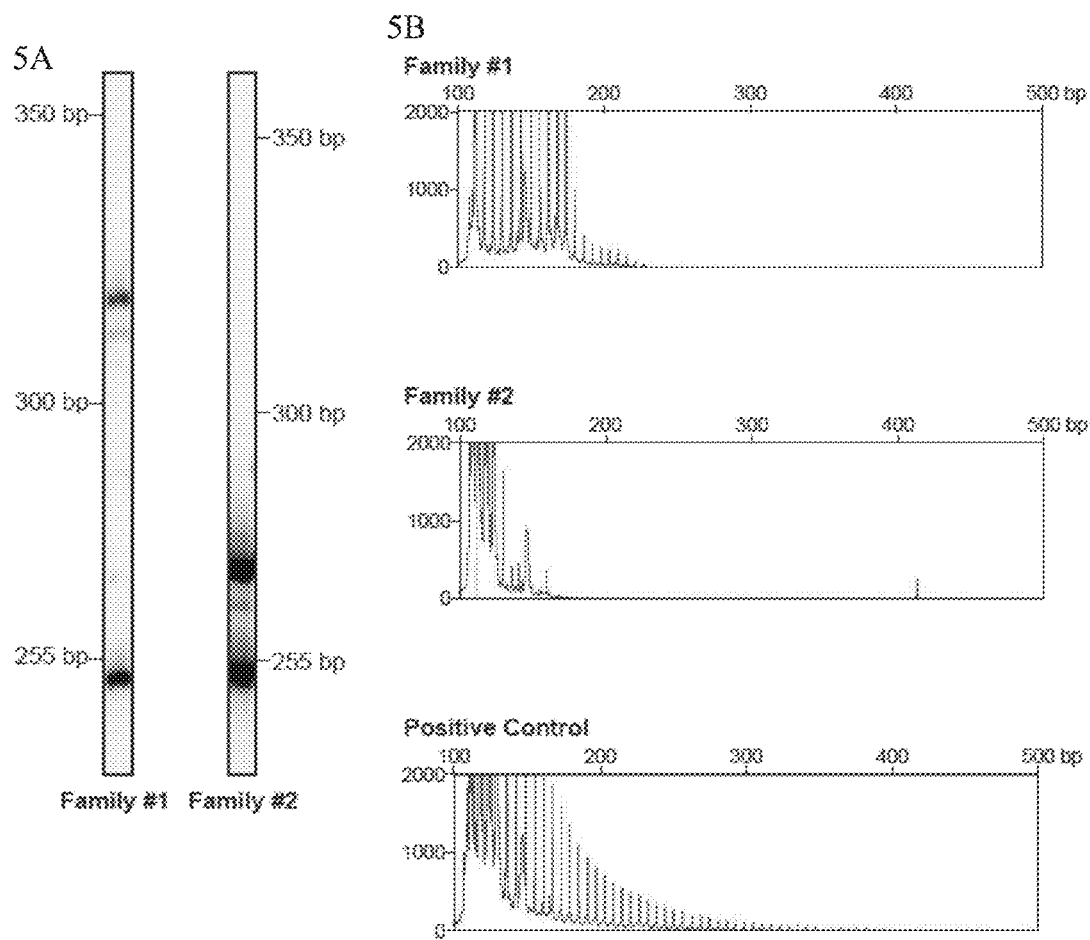
FIGS. 5A-5B: C9orf72 does not contain a repeat expansion in families subject to exome sequencing. 5A: The repeat region of c9orf72 was amplified in affected family members from Family #1 and #2 using primers outside the repeat region. The PCR products were separated by PAGE. Both families were shown to be heterozygous thus lacking the repeat expansion. The estimated number of repeats was 3 and 14 for Family #1 and 3 and 6 for Family #2. 5B: Repeat expansion PCR was used to amplify the repeat region of c9orf72 in Family #1 and #2. Both families failed to display an extended repeat expansion. A positive control is shown for comparison. Linkage analysis revealed a negative LOD score at c9orf72 supporting these results.
Figure 6:
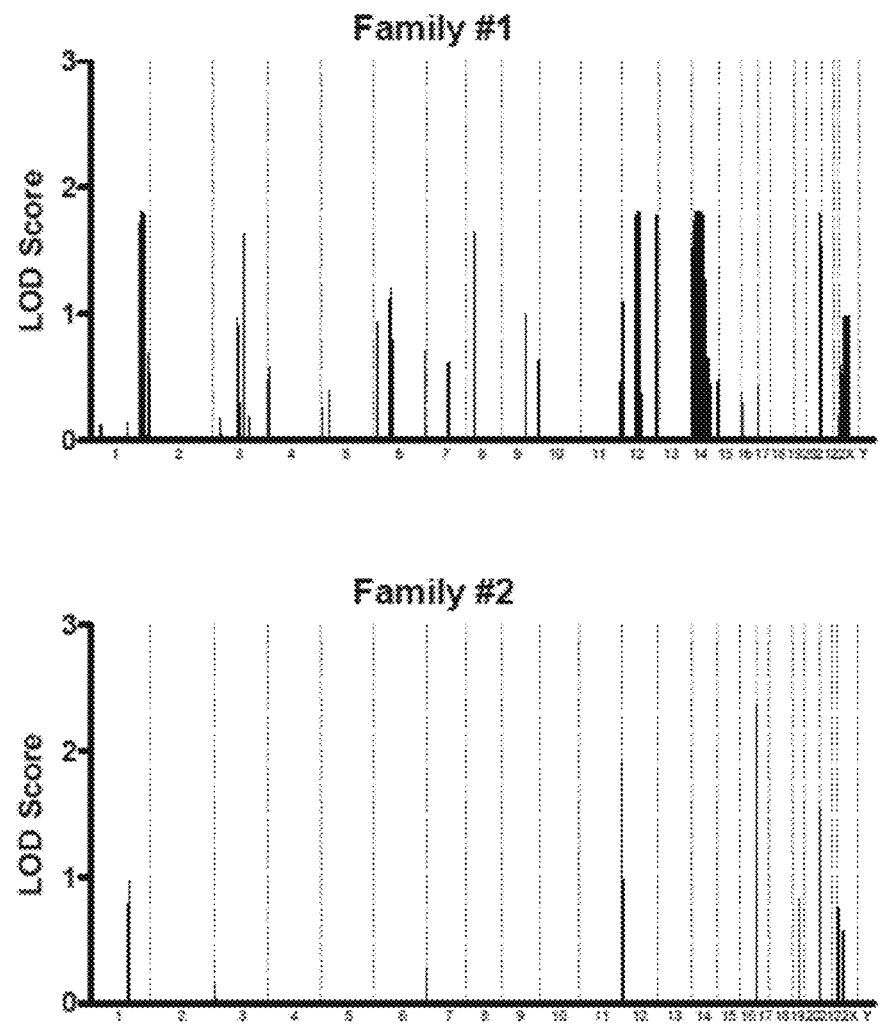
FIG. 6: Linkage analysis of families displaying ALS. Linkage peaks were identified by subjecting DNA to genome-wide genotyping using the Affymetrix 10K SNP arrays and analyzed using the software application Allegro v.2.0 to generate multi-point LOD scores. Only affected members (and married-in samples) were used for the analysis. SNPs identified from exome sequencing located in regions with a negative LOD score were eliminated as a candidate causal mutation for ALS.

To identify causative genes for familial ALS, exome capture followed by deep sequencing was performed on two large ALS families (FIGS. 1A, 1B) of Caucasian (family 1) and Sephardic Jewish (family 2) origin. Both display a dominant inheritance mode and are negative for known ALS-causing mutations, including the newly identified hexanucleotide repeat expansion in C9orf72 (DeJesus-Hernandez, M. et al. Neuron 72, 245-256 (2011); Renton, A. E. et al. Neuron 72, 257-268 (2011); Gijselinck, I. et al. Lancet Neurol. 11, 54-65 (2012); FIGS. 5A-5B). For each family, two affected members with maximum genetic distance were selected for exome sequencing. A high level of coverage (>150×) was achieved with an average of $1.1 \times 10^{10}$ and $2.3 \times 10^{10}$ base pairs sequenced for members of families 1 and 2, respectively (Tables 1 and 2). To identify candidate causative mutations, variants were identified and filtered, as in previous exome sequencing reports (Johnson, J. O. et al. Neuron 68, 857-864 (2010)), using several criteria: the variant is observed in both family members, alters the amino acid sequence, is not excluded by linkage analysis (FIG. 6), and is absent from dbSNP132, the 1000 Genomes Project (May 2011 release) or the National Heart, Lung, and Blood Institute (NHLBI) Exome Sequencing Project (ESP) Exome Variant Server (5,379 sequenced exomes; evs.gs.washington.edu/EVS/). Remaining variants were confirmed by Sanger sequencing and tested for Mendelian segregation in all affected family members. The resulting number of candidate causative mutations identified was two within family 1 and three within family 2 (Tables 3 and 4). Interestingly, the two families contain different mutations (C71G and M114T) within a single common gene: PFN1, located on chromosome 17p13.2. PFN1 is an 140-amino-acid protein and major growth regulator of filamentous (F)-actin through its binding of monomeric (G)-actin (Mockrin, S C & Korn E D, Biochem, 19:5359-5362 (1980)). On the basis of these data, the hypothesis that PFN1 gene mutations cause familial ALS was tested.

FIGS. 1A-1D show sequence analysis of all available members of families 1 and 2. All four affected members of family 1 for which DNA was available possess the PFN1 (C71G) variant. A single obligate carrier of the C71G variant (III:13) did not develop disease; however, death occurred before the average age of onset of this family (Table 5). All unaffected family 1 members displayed the wild-type genotype (FIG. 1A). Within family 2, all eight affected members for which DNA was available contained the M114T variant. On the basis of the genotypes of spouse and progeny (not shown), it was confirmed that a ninth affected family member (III:2) also carries the mutation. Of 7 unaffected members, 5 do not contain the M114T variant. One unaffected mutation carrier is now in their mid-40s (III:15) and a second obligate carrier (II:4) was asymptomatic into their 70s (FIG. 1B). The results herein indicate that these mutations have a high degree of penetrance. Affected-only linkage analysis of the PFN1 variants in family 1 and 2 yielded a logarithm of the odds (lod) scores of 1.80 and 2.71, respectively.

Figure 7:
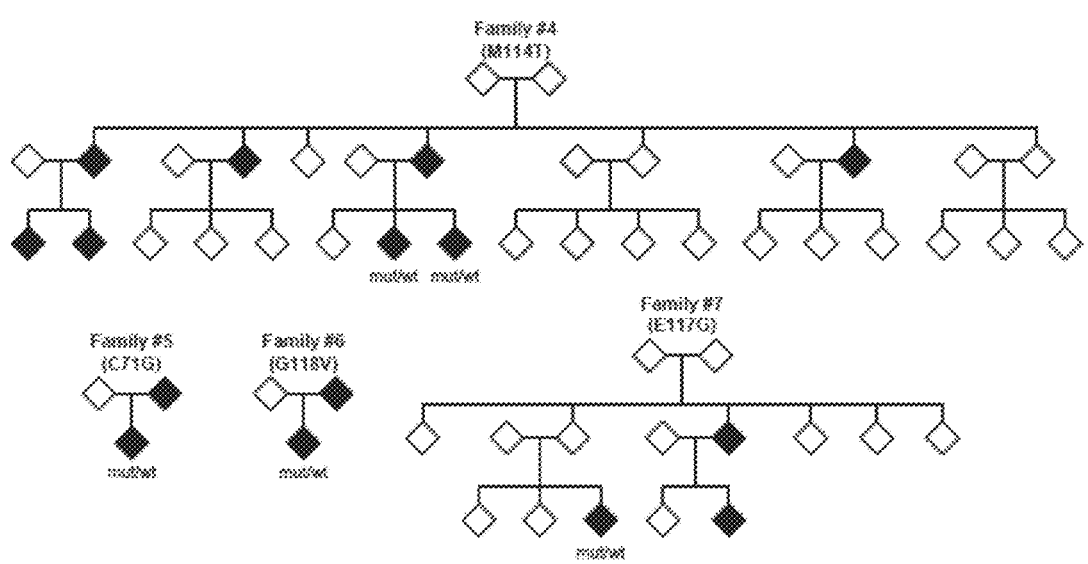
FIG. 7: Pedigrees of families with PFN1 mutations. Pedigrees of Families #4-7, which harbor PFN1 mutations, are shown. Genotypes of available samples are shown.
Figure 8:
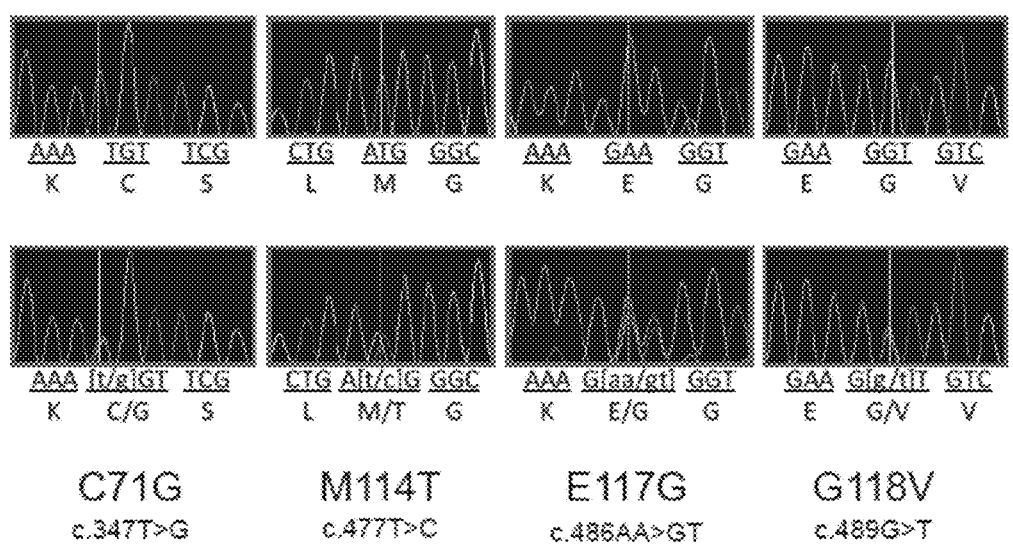
FIG. 8: Chromatograms of PFN1 mutations. Sequence traces of representative samples harboring either wild-type (top row) or mutant (bottom row) PFN1 are shown. Base pair changes are based on UCSC accession number: uc002gaa.3.

To determine whether PFN1 mutations cause familial ALS, the coding region was sequenced in a panel of 272 further FALS cases prescreened for common causative mutations. Five other familial ALS cases containing alterations in the PFN1 gene (FIGS. 7 and 8) were identified. Interestingly, the C71G alteration originally identified in family 1 was discovered in two other families. For one of these families (family 3), DNA was available for three other affected family members. Sequencing of these samples showed that the mutation co-segregates with ALS (FIG. 1C). A single unaffected member of the family (IV:2) also contains the mutation; the current age of this family member is mid-40s. Affected-only linkage analysis of family 3 yielded a lod score of 1.50 and a combined lod score of 6.01 for families 1-3. A second M114T mutation was identified in an ALS family of Italian origin (family 4, FIG. 7). DNA available for one sibling was shown by sequencing to contain this mutation. PFN1 variants were observed in two other FALS cases: a consecutive base-pair change (AA to GT) resulting in an E117G mutation, and a G-to-T transversion resulting in a G118V mutation (FIGS. 7 and 8). DNA was not available from other family members for these cases. Sequencing of the PFN1 coding region in 816 sporadic ALS (SALS) samples identified two samples containing the E117G mutation. No further non-synonymous changes were identified in the FALS and SALS samples (Table 6). Haplotype analysis using surrounding single nucleotide polymorphisms (SNPs) indicates that the C71G mutation derives from a single ancestral mutation (Table 7).

To confirm further that the newly identified variants (E117G and G118V) represent causal mutations, not benign polymorphisms, each was interrogated in the 1000 Genomes Project database and the NHLBI ESP Exome Variant Server. The G118V mutation was not identified in either database.

However, the E117G variant was observed in 2 samples out of 5,379 at the NHLBI ESP Exome Variant Server. This analysis was extended by genotyping all mutations in an independent set of 1,089 control samples. Three of the mutations (C71G, M114T and G118V) were not observed in the 1,089 control samples; however, the E117G variant was observed in a single control (Table 8). By combining data from the 1000 Genome Project, the NHLBI ESP Exome Variant Server and independent genotyping, three of the ALS-linked variants were not present in 7,560 control samples (15,120 alleles), whereas the fourth (E117G) was found in 3 out of 1,090 ALS cases and in 3 out of 7,560 control samples ($2.75 \times 10^{-3}$ versus $3.97 \times 10^{-4}$; P=0.030, two-tailed Fisher's exact test). Thus, it is likely that the E117G variant is either non-pathogenic or, more likely, represents a less pathogenic mutation.

In total, 4 mutations in 7 out of 274 FALS cases were identified. In each case, the altered amino acid was evolutionarily conserved down to the level of zebrafish (FIG. 1D), supporting the likelihood that these mutations are pathogenic. The age of onset for FALS cases with PFN1 mutations is 44.8±7.4 (Table 5). All PFN1 mutant cases displayed limb onset; no bulbar onset was observed (n=22, Table 5). Given that bulbar onset represents ~25% of ALS cases (Landers, J. E., et al., Proc. Natl. Acad. Sci., USA, 106: 9004-9009 (2009)), this result indicates a common clinical phenotype among patients with PFN1 mutations.

Figures 2A, 2B, 2C, 2D, 2E, 2F:
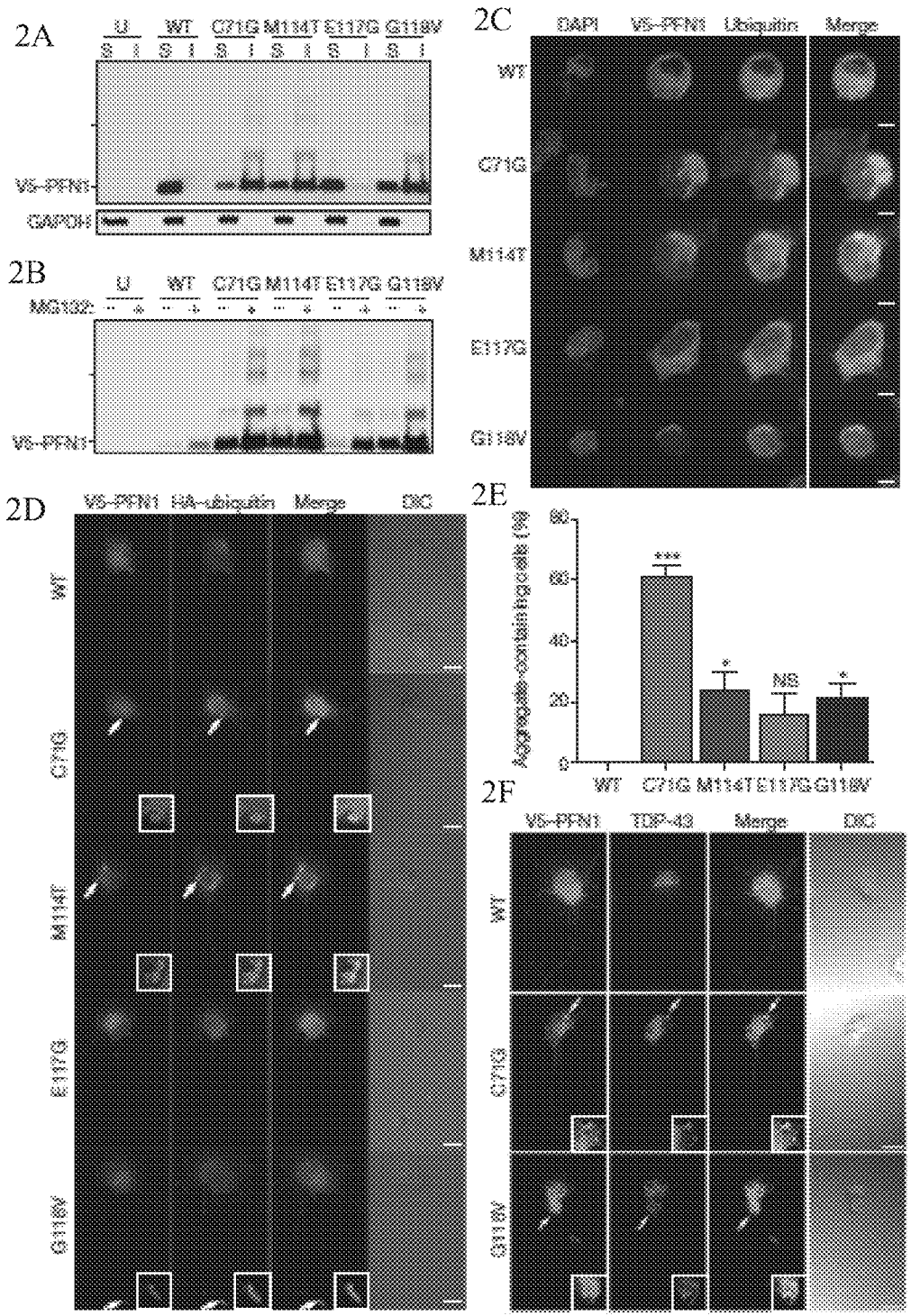
FIGS. 2A-2F: Mutant PFN1 produces ubiquitinated insoluble aggregates. 2A: Western blot analysis of transfected N2A cells subject to NP-40-soluble (S) and insoluble (I) fractionation. U, untransfected; WT, wild-type. 2B: Transfected cells were treated with MG132 and processed as in a. Tick marks indicate 20-kDa and 37-kDa markers. 2C, 2D: Transfected N2A cells (c) and transfected PMNs (d) were stained with V5, haemagglutinin (HA) (PMNs) and ubiquitin (N2A) antibodies. Example aggregates are enlarged in the insets in d. DAPI, 49, 6-diamidino-2-phenylindole; DIC, differential interference contrast. 2E: Transfected N2A cells displaying insoluble aggregates were counted and analysed using one-way analysis of variance (ANOVA) testing with Dunnett's multiple test comparison (n5127-135 transfected cells from three independent experiments). *P, 0.05; ***P, 0.001; NS, not significant (P.0.05). Error bars indicate s.e.m. 2F: Transfected PMNs stained with V5 and TDP-43 antibodies. Scale bars, 5 mm (2C) and 10 mm (2D, 2F).
Figure 9:
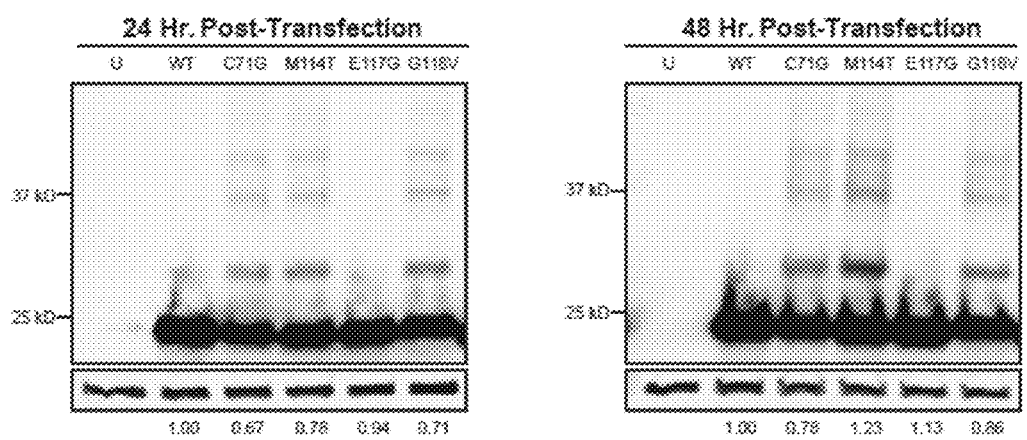
FIG. 9: Relative expression of transfected wild-type and mutant PFN1 in N2A cells. N2A cells were transfected with constructs expressing wild-type or mutant V5-PFN1. At the indicated time points, the cells were lysed in buffer containing 3% SDS/8 M urea. The lysates were subject to Western blot analysis with antibodies to V5 and GAPDH. Quantification was performed using the signal from the entire lane for V5. The relative expression of V5-PFN1 is shown.
Figure 10:
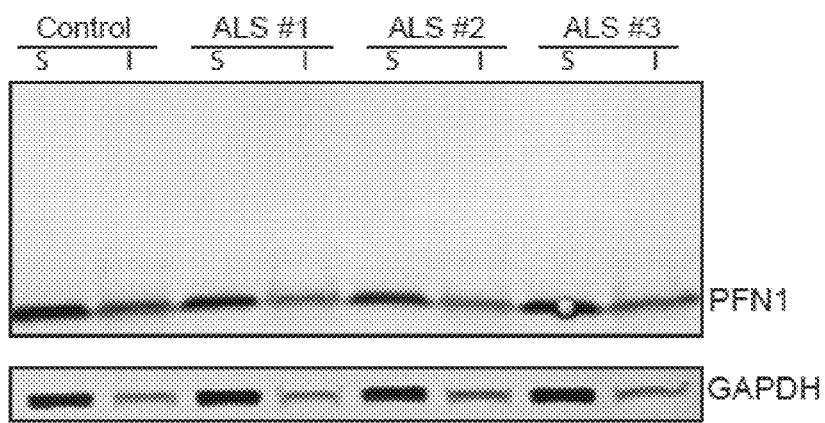
FIG. 10: Lymphoblast derived from ALS patients with PFN1 mutations do not display increased insoluble aggregates. Lymphoblasts from three affected and one unaffected member of Family #1 were subject to NP-40-soluble (S) and insoluble (I) fractionation followed by a Western blot analysis using antibodies directed against PFN1 or GAPDH. The affected members harbor a C71G mutation in the PFN1 gene. As shown, no increased insoluble PFN1 protein was observed in the ALS samples relative to the control family member.

Ubiquitinated, insoluble aggregates are pathological hallmarks of several neurodegenerative diseases including ALS, Parkinson's disease and Alzheimer's disease. To investigate whether the observed PFN1 mutants form insoluble aggregates, western blot analysis of NP-40-soluble and insoluble fractions was performed on Neuro-2A (N2A) cells transfected with wild-type or one of the four PFN1 mutants. PFN1 protein was present predominantly in the soluble fraction of cells transfected with the wild-type construct as compared with the insoluble fraction (FIG. 2A). Conversely, a considerable proportion of the C71G, M114T and G118V mutant proteins were detected in the insoluble fraction. Furthermore, several higher molecular mass species were observed, indicative of SDS-resistant PFN1 oligomers. However, the E117G mutant displayed a pattern more similar to wild-type PFN1 with most of the expressed protein in the soluble fraction. Differential expression of PFN1 constructs was ruled out by western blot analysis of whole cell lysates (FIG. 9). Analysis of lymphoblast cell lines derived from affected and unaffected members of family 1 did not display any differences in PFN1 protein solubility (FIG. 10). Autopsy material was not available for any affected individual.

Figure 11:
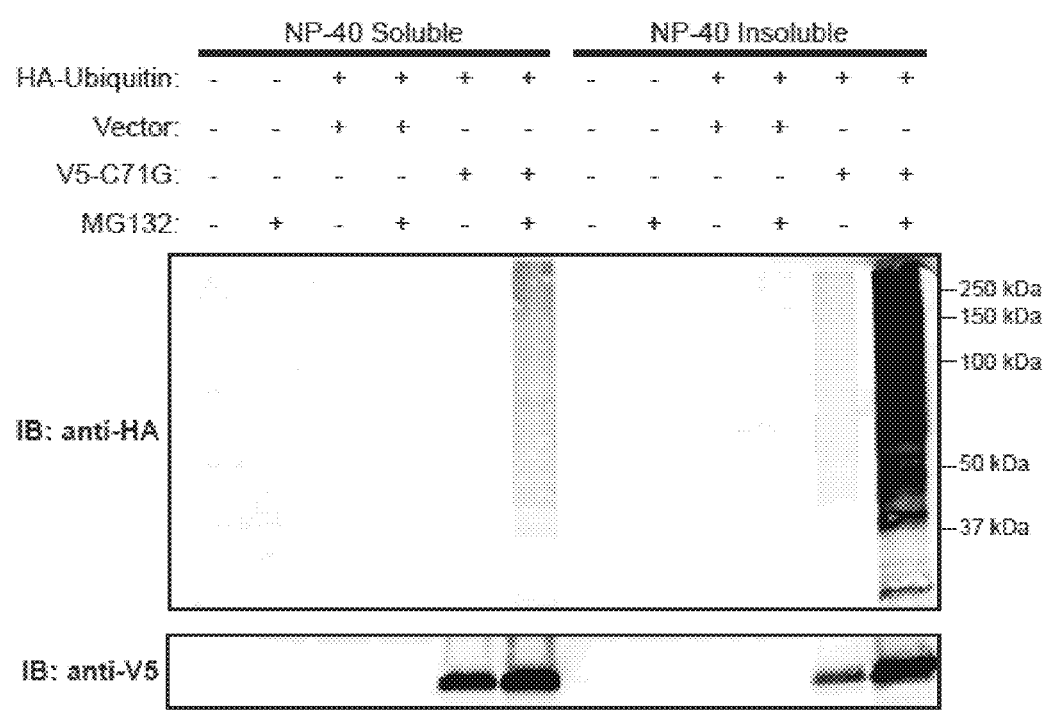
FIG. 11: Insoluble mutant PFN1 is polyubiquitinated. N2A cells were transfected with control vector (lanes 3, 4, 9, 10), V5-PFN1-C71G (lanes 5, 6, 11, 12) and a HA-tagged Ubiquitin expressing vector (lanes 3-6, 9-12). The cells were treated with (lanes 2, 4, 6, 8, 10, 12) and without (lanes 1, 3, 5, 7, 9, 11) the proteasome inhibitor MG132. The cells were then lysed and NP-40 soluble (lanes 1-6) and insoluble (lanes 7-12) were isolated and immunoprecipitated with a V5 antibody. The immunoprecipitates were separated by SDS-PAGE and then immunoblotted with antibodies for either V5 or HA, as indicated.

These observations were extended by staining the PFN1 protein in transfected cells. Wild-type PFN1 exhibited a diffuse cytoplasmic expression pattern in transfected N2A cells (FIG. 2C), as previously reported (Suetsugu, S. et al. EMBO J. 17, 6516-6526 (1998)). By contrast, ALS-linked PFN1 mutants often assembled into cytoplasmic aggregates. Image analysis determined that 15-61% of mutant-expressing cells contain cytoplasmic aggregates, including the E117G mutant, which showed minimal insoluble PFN1 protein by western blot analysis. No aggregates were observed for cells expressing wild-type PFN1 (FIG. 2E). Co-staining revealed that these aggregates were also ubiquitinated. Primary motor neurons (PMNs) expressing the C71G, M114T and G118V mutants similarly demonstrated ubiquitinated aggregates, albeit at a lower percentage (FIG. 2D); aggregates were not observed in cells expressing the E117G mutant or wild-type PFN1. Immunoprecipitation of the PFN1 protein followed by western blot analysis confirmed that the insoluble mutant PFN1 protein is polyubiquitinated (FIG. 11).

Figure 12:
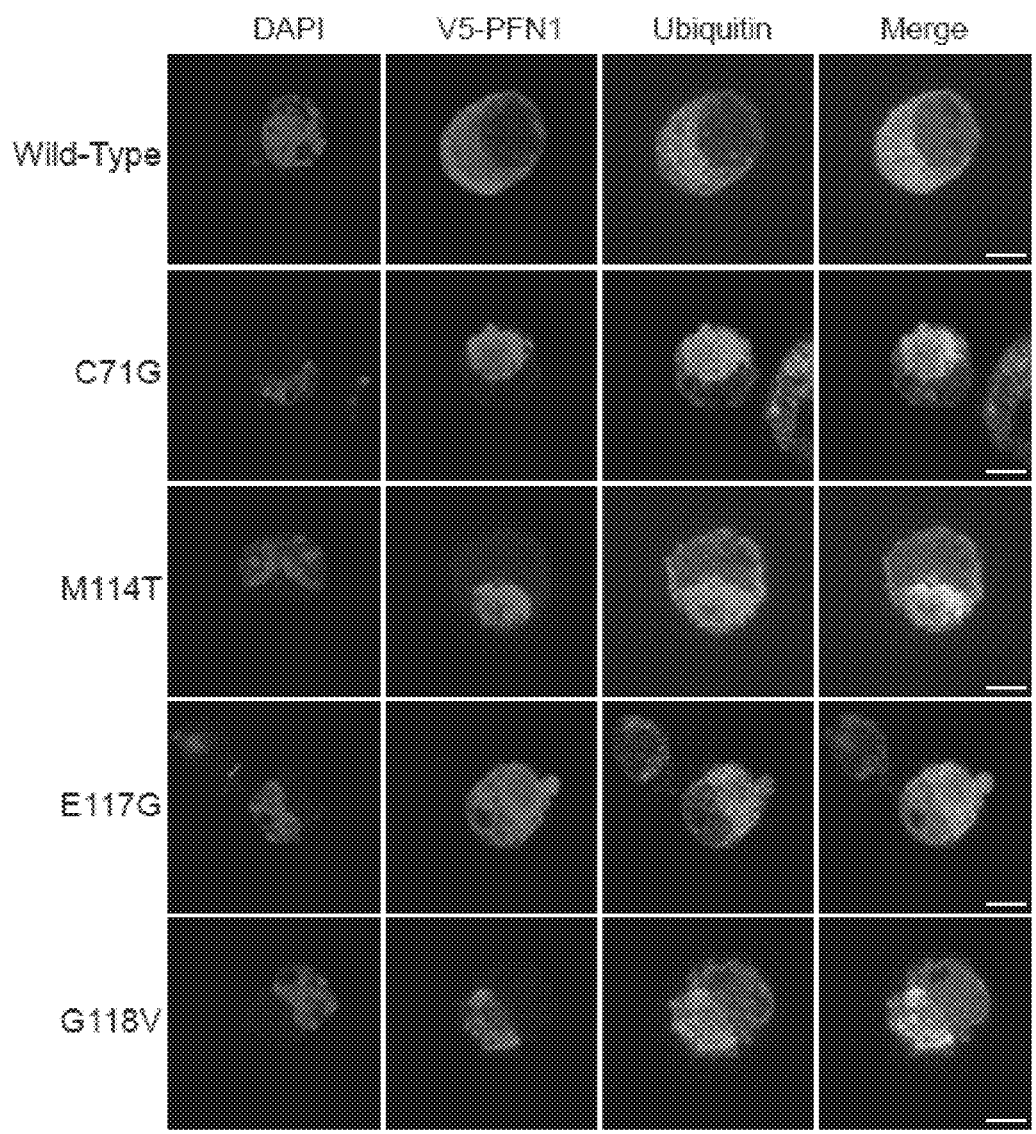
FIG. 12: Cellular staining of PFN1 mutants in N2A cells exposed to MG132. N2A cells were transfected with constructs expressing wild-type or mutant V5-PFN1. At 24 hours post-transfection, cells were exposed to 10 µM MG132 for an additional 24 hours. The cells were then fixed and stained for V5-PFN1 and ubiquitin localization. Scale: 5 µM.
Figure 13:
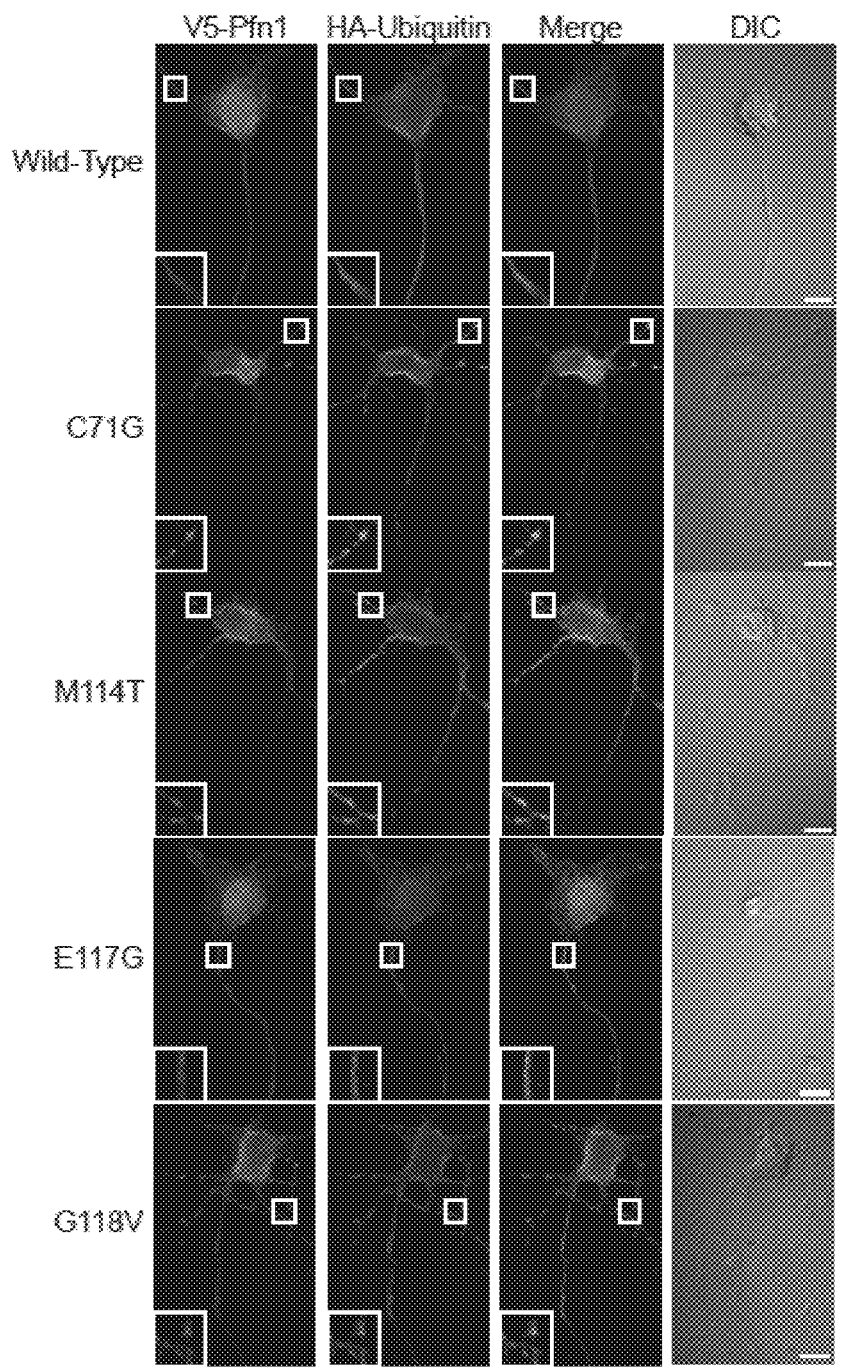
FIG. 13: Cellular staining of PFN1 mutants in primary motor neurons exposed to MG132. Primary motor neurons were transfected with constructs expressing either wild-type or mutant V5-PFN1. Additionally, the PMNs were co-transfected with a HA-ubiquitin expressing construct. Twenty-four hours post transfection, cells were exposed to 10 µM MG132 for an additional 12 hours. The cells were then fixed and stained with anti-V5 and anti-HA antibodies. Scale: 10 µm.
Figure 14:
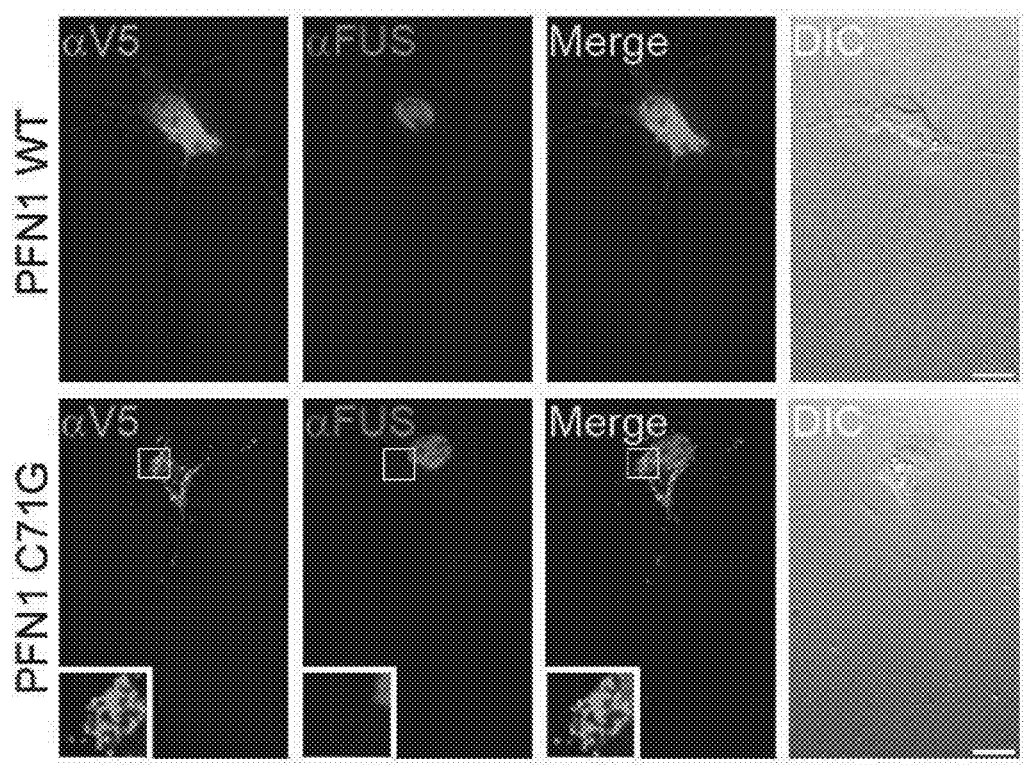
FIG. 14: Mutant PFN1 does not co-aggregate with FUS. Primary motor neurons were transfected with constructs expressing either wild-type or mutant V5-PFN1. At twenty-four hours post transfection, the cells were fixed and stained with anti-V5 and anti-FUS antibodies. As shown, no co-aggregation of FUS with mutant PFN1 was observed. Scale: 100 µm.
Figure 15:
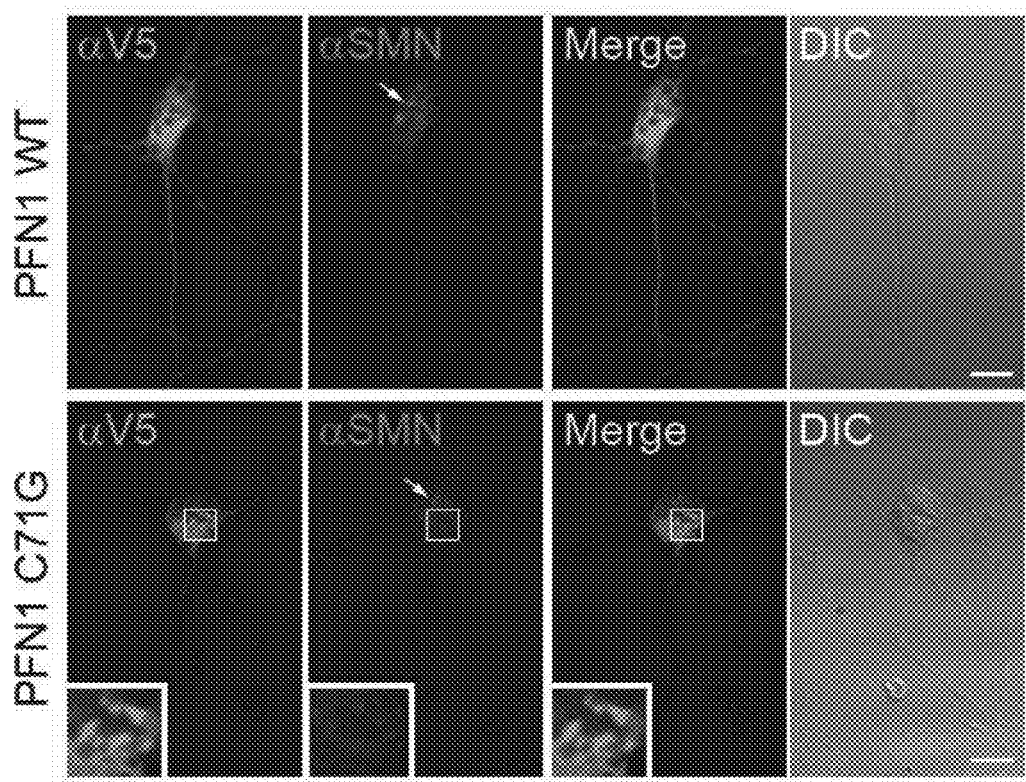
FIG. 15: Mutant PFN1 does not co-aggregate with SMN. Primary motor neurons were transfected with constructs expressing either wild-type or mutant V5-PFN1. At twenty-four hours post transfection, the cells were fixed and stained with anti-V5 and anti-SMN antibodies. As shown, no co-aggregation of SMN with mutant PFN1 was observed. Arrows indicate the location of nuclear gems. Scale: 100 µm.
Figure 16:
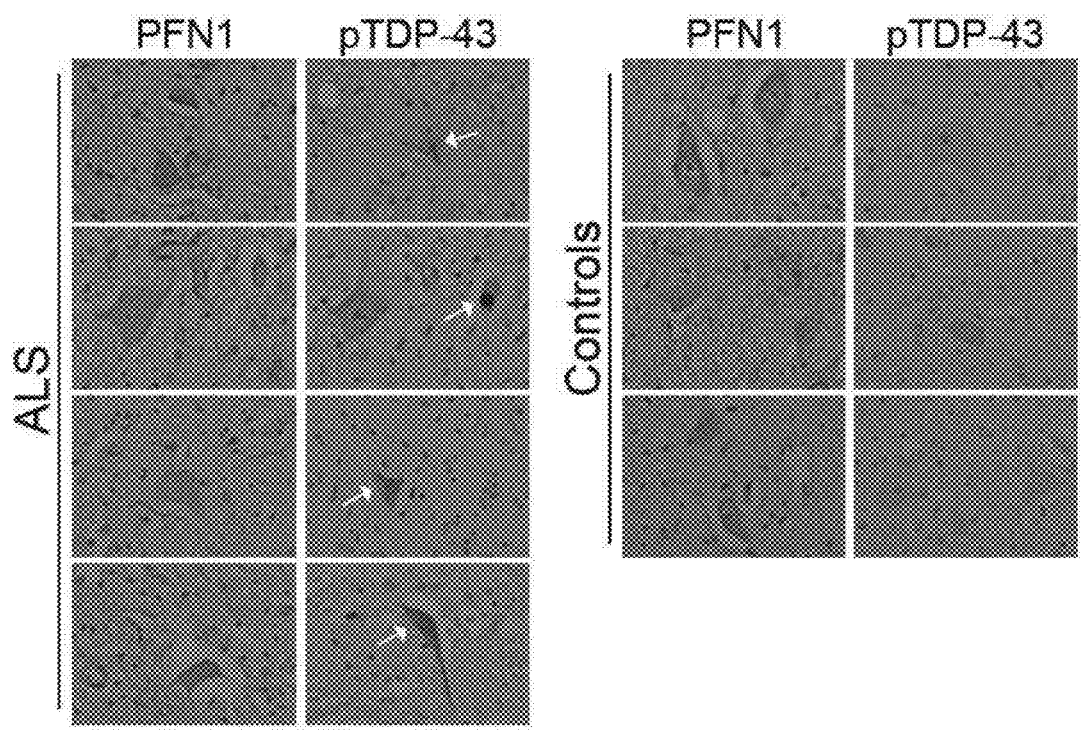
FIG. 16: Immunohistochemistry of PFN1 and pTDP-43 in spinal cord tissue. PFN1 and pTDP-43 protein were stained in spinal cord tissues derived from 18 SALS cases displaying TDP-43 pathology and 6 non-ALS controls without TDP-43 pathology. Representative images of 4 cases and 3 controls are shown. These results failed to identify abnormal PFN1 pathology in the SALS cases relative to control tissue.
Figure 17:
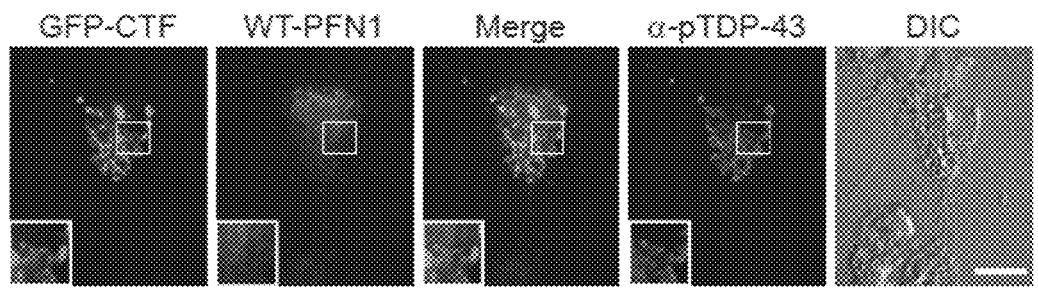
FIG. 17: TDP-43 aggregates do not co-localize with wild-type PFN1. Primary motor neurons were co-transfected with constructs expressing wild-type V5-PFN1 and a GFP-labelled C-terminal fragment of TDP-43, previously shown to produce cellular aggregates. At twenty-four hours post transfection, the cells were fixed and stained with anti-V5 and anti-pTDP-43 antibodies. Scale: 100 µm.

To determine whether ubiquitin-proteosome system impairment causes accumulation of mutant PFN1 aggregates, transfected N2A cells were exposed to the proteasome inhibitor MG132. ALS-linked PFN1 mutants, including E117G, showed increased insoluble protein levels and increased levels of higher molecular mass species by western blot analysis. Minimal insoluble protein was observed for the wild-type PFN1 protein (FIG. 2B). PFN1 staining in N2A cells and PMNs confirmed these results. Cells expressing C71G, M114T and G118V mutant PFN1 had numerous, large aggregates after MG132 treatment. E117G mutants showed a moderate aggregate level, and the wild-type protein displayed minimal levels (FIGS. 12 and 13). Given the propensity of mutant PFN1 to form aggregates, whether other ALS-related proteins are present within these aggregates was investigated. Thus, PMNs were transfected with mutant PFN1 and tested for alterations in the cellular localization of the ALS-related proteins FUS and TDP-43. Furthermore, alterations in the spinal muscular atrophy-related protein SMN owing to its ability to bind PFN1 (Giesemann, T. et al. J. Biol. Chem. 274, 37908-37914 (1999)) were also investigated. No co-aggregation of either FUS or SMN with mutant PFN1 was observed (FIGS. 14 and 15). However, ~30-40% of cells contained cytoplasmic PFN1 aggregates co-stained with TDP-43 (FIG. 2F). These results indicate that mutant PFN1 may contribute to ALS pathogenesis by inducing aggregation of TDP-43. On the basis of these observations, whether aggregates of TDP-43 contain PFN1 were investigated by staining spinal cord tissues from 18 SALS cases displaying TDP-43 pathology and 6 non-ALS controls without TDP-43 pathology (FIG. 16). Abnormal PFN1 pathology was not discovered in SALS cases, indicating that TDP-43 aggregation does not induce PFN1 aggregation. Expression of the carboxy-terminal fragment of TDP-43, which produces insoluble aggregates, in PMNs also failed to co-aggregate wildtype PFN1, thus supporting this observation (FIG. 17).

Figures 3A, 3B, 3C, 3D:
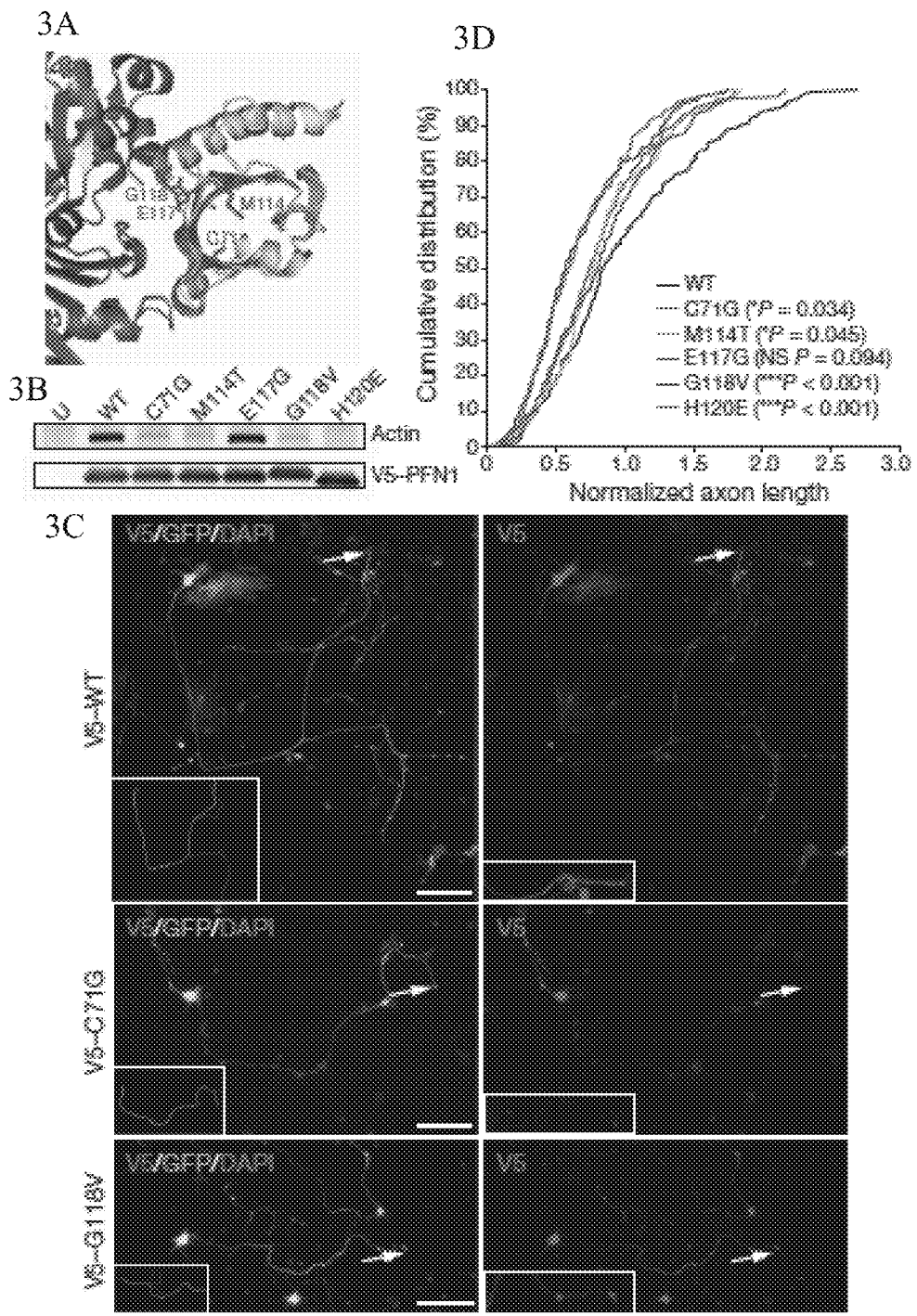
FIGS. 3A-3D: Mutant PFN1 inhibits axon outgrowth. 3A: PFN1-actin interaction region (Protein Data Bank accession 2BTF) using the PyMOL Molecular Graphics System (v.1.4). Magenta: actin; yellow: PFN1; green: actin-binding PFN1 residues; red: ALS-linked mutated PFN1 residues. 3B: Transfected HEK293 cells were immunoprecipitated with a V5 antibody and then immunoblotted with antibodies for either V5-PFN1 or actin. 3C: PMNs transfected with wild-type or mutant V5-PFN1 and a green fluorescent protein (GFP)-expressing construct were stained to detect V5-PFN1. The axon tip, indicated by arrows, is enlarged in the inset, right panel. Scale bars, 100 mm. 3D: Cumulative distribution of axon lengths relative to the mean of wild-type PFN1-transfected cells was plotted. P values are given in the legend (n5104-161 cells from four independent experiments).

Evaluation of the PFN1-actin complex crystal structure showed that all ALS-linked mutations lie in close proximity to actin-binding residues of PFN1 (Schutt, C. E. et al. Nature, 365, 810-816 (1993); FIG. 3A). Therefore, whether the ALS-linked mutations display a decreased level of bound actin was investigated. Towards this end, immunoprecipitation and western blot analysis of cells transfected with wild-type and mutant PFN1 were performed. As a control, cells were also transfected with a construct expressing a synthetic PFN1 (H120E) mutant protein. This alteration is located at a crucial residue previously shown to abolish PFN1 binding to actin (Suetsugu, S. et al. EMBO J. 17, 6516-6526 (1998)). It was observed that C71G, M114T, G118V and H120E mutants had reduced levels of bound actin relative to wild-type PFN1 (FIG. 3B). The E117G mutant did not show a reduction of bound actin relative to wild-type PFN1.

Previous reports have shown that PFN1 protein alterations inhibit neurite outgrowth (Suetsugu, S. et al. EMBO J. 17, 6516-6526 (1998); Wills, Z. et al. Neuron 22, 291-299 (1999)). Whether ALS-linked PFN1 mutants inhibit neurite outgrowth was investigated by measuring axonal length in PMNs transfected with wild-type or mutant PFN1. As a positive control, PMNs were also transfected with the H120E-expressing construct. In addition to lacking actin-binding ability, the H120E protein inhibits neurite outgrowth (Suetsugu, S. et al. EMBO J. 17, 6516-6526 (1998)). As expected, the H120E-expressing cells displayed a pronounced decrease in axon length relative to the wild-type construct (FIG. 3D). Three ALS-linked PFN1 mutations (C71G, M114T and G118V) also showed a significant decrease in axon outgrowth (FIG. 3C, 3D). In particular, the G118V-associated reduction is similar to that observed with the H120E construct. Axon outgrowth inhibition was observed with the E117G mutant but did not reach statistical significance. These results indicate that mutations in PFN1 contribute to ALS pathogenicity, in part, by inhibiting axon dynamics.

Figures 4A, 4B, 4C:
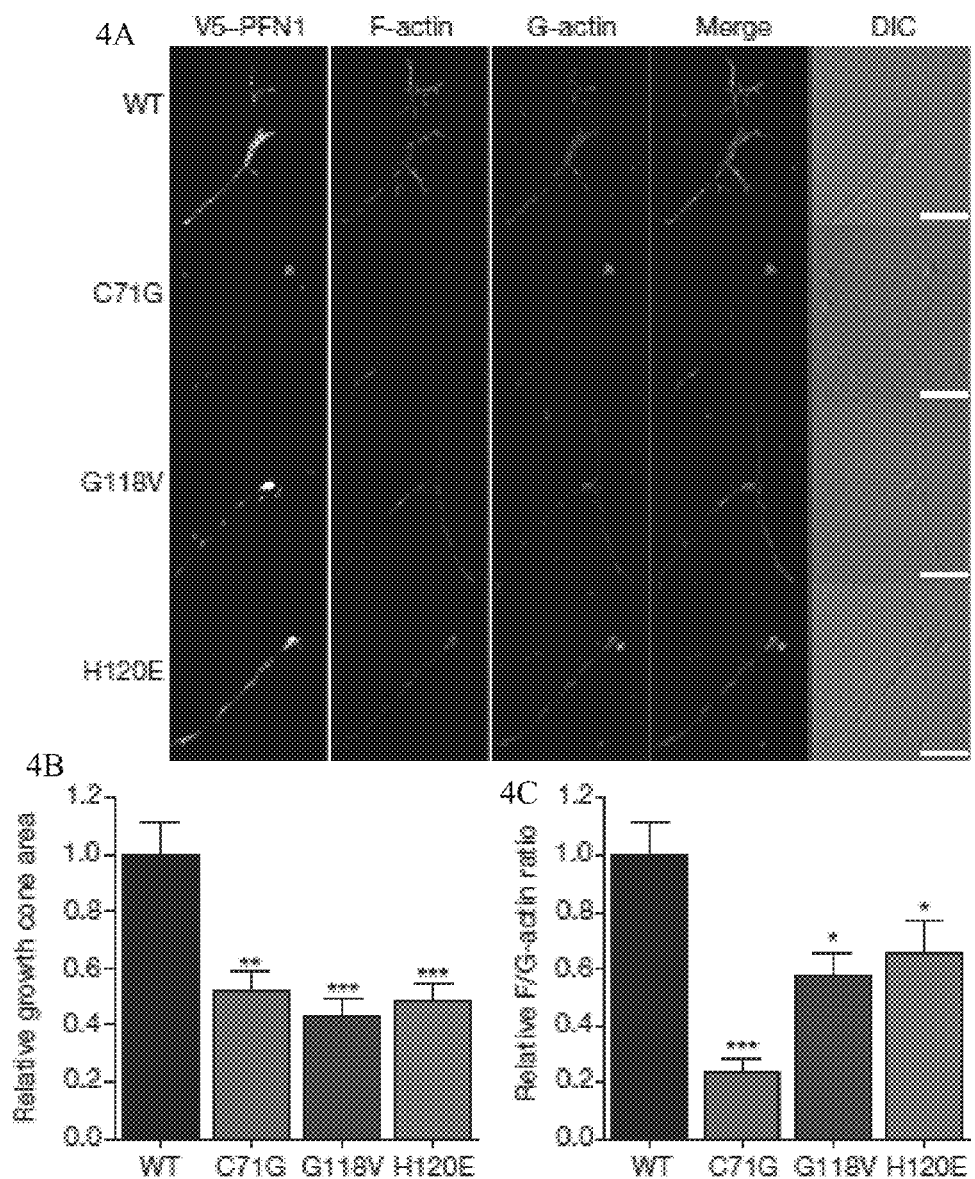
FIGS. 4A-4C: Mutant PFN1 reduces growth cone size and F/G-actin expression. 4A: PMNs were transfected with either wild-type or mutant V5-PFN1. At 3 days after transfection, cells were fixed and stained to detect V5-PFN1, F-actin (phalloidin, red) and G-actin (DNase I, green). The growth cone region of representative cells is shown. Scale bars, 10 mm. 4B, 4C: The growth cone area (4B) and F/G-actin expression (4C) of transfected cells were determined and plotted. Comparisons to the wild-type V5-PFN1-transfected cells were made using one-way ANOVA testing. *P, 0.05; P, 0.01; *P, 0.001 (n527-35 cells from three independent experiments). Error bars indicate s.e.m.

The regulation of actin dynamics in the growth cone is necessary for axon outgrowth. Defects in PFN1 are associated with growth cone arrest and reduced axon outgrowth in embryonic motor neurons of Drosophila (Wills, Z. et al. Neuron 22, 291-299 (1999)). To determine whether ALS-linked PFN1 mutants have a similar phenotype, PMNs transfected with wild-type and two mutant PFN1 constructs (C71G and G118V) were stained to detect F- and G-actin localization patterns in the highly dynamic and actin-rich growth cone. These mutants were selected owing to their greater influence on axon outgrowth. PFN1 mutant expression in PMNs led to a significantly reduced growth cone size (~43-52%) relative to wildtype PFN1 (FIG. 4B). Also, mutant PFN1 expression significantly altered growth cone morphology. In wild-type PFN1-expressing cells, growth cones had elaborate structures with several F-actin rich filopodia (FIG. 4A), whereas virtually no filopodia were visible in the mutant PFN1 growth cones. Similar results were observed for the synthetic H120E mutant defective in actin binding. The growth cones in mutant-expressing PMNs also had a lower ratio of F/G-actin relative to wild-type-expressing PMNs (FIG. 4C). In particular, the C71G mutant-expressing PMNs displayed an F/G-actin ratio 24.4% of the wild-type expressing PMNs. These results indicate that mutant PFN1 can inhibit the conversion of G-actin to F-actin within the growth cone region, thus affecting its morphology.

PFN1 expression is ubiquitous in non-muscle cells, whereas PFN2 is expressed in brain and neuronal tissues (Witke, W. et al. EMBO J. 17, 967-976 (1998)), and PFN3 in the testis (Braun, A. et al. Gene 283, 219-225 (2002)). To determine whether mutations in PFN2 or PFN3 may also contribute to FALS, the entire coding sequence of both genes in 274 FALS cases was sequenced. In contrast to PFN1, no non-synonymous alterations were observed in these FALS cases (Table 6), which suggests that PFN2 and PFN3 mutations are not an important cause of FALS.

As described herein, exome sequencing was applied to two large families displaying ALS. Through this approach, the number of causal candidates in each family was restricted to two and three genes. Fortuitously, both families had mutations in the same gene, PFN1. Although the possibility that mutations in other candidate genes may be causative cannot be ruled out, several lines of evidence demonstrate PFN1 as the causative gene. First, a further five families with mutations in the PFN1 gene, including a third large family in which we confirmed segregation of the mutations, were identified. Second, mutant PFN1 displayed aggregation propensities analogous to those of other proteins implicated in neurodegenerative diseases such as ALS. Third, the mutants displayed several functional differences compared with the wild-type protein, including a lower bound actin level, an axonal outgrowth inhibition, and growth cone size reduction. Taken together, these results strongly indicate that mutations in the PFN1 gene cause familial ALS.

PFN1 is an intensely studied protein owing in part to its regulation of actin polymerization. PFN1 promotes nucleotide exchange on actin, converting monomeric ADP-actin to ATP-actin (Mockrin, S. C. & Korn, E. D. Biochemistry 19, 5359-5362 (1980). PFN1-ATP-actin complexes can bind to the fast-growing end of actin filaments. Dissociation of the complex allows the ATP-actin monomer to be added to the growing actin filament (Tilney, L. G. et al. J. Cell Biol. 97, 112-124 (1983)). Shown herein is that mutant PFN1 contributes to ALS pathogenesis by altering actin dynamics and inhibiting axon outgrowth. Similarly, expression of either mutant SOD1 (Takeuchi, H. et al. Brain Res. 949, 11-22 (2002)) or mutant TDP-43 (Duan, W. et al. Brain Res. 1397, 1-9 (2011)) inhibits neurite outgrowth, and primary neurons from FUS-deficient mice have reduced spine numbers and abnormal morphology (Fujii, R. et al. Curr. Biol. 15, 587-593 (2005)). These observations indicate a common pathogenic feature among diverse ALS genes. However, there is also the possibility that alterations to other PFN1 functions contribute to the pathogenesis. PFN1 is also a complex regulator of cellular processes through its interactions with several proteins. Indeed, it has been shown to interact directly with more than 50 proteins (Witke, W. Trends Cell Biol. 14, 461-469 (2004)). Of interest, PFN1 directly interacts with three proteins that, when mutated, cause neurodegenerative disease—VCP (ALS-frontotemporal dementia, inclusion body myositis and Paget's disease) (Witke, W. et al. EMBO J. 17, 967-976 (1998)); SMN (spinal muscular atrophy) (Giesemann, T. et al. J. Biol. Chem. 274, 37908-37914 (1999)); and HTT (Huntington's disease) (Shao, J. et al. Mol. Cell. Biol. 28, 5196-5208 (2008)).

There is increasing evidence that cytoskeletal defects have a major role in motor neuron diseases. Rarely, mutations in genes encoding neurofilament heavy polypeptide (NEFH) (Al-Chalabi, A. et al. Hum. Mol. Genet. 8, 157-164 (1999)), peripherin (PRPH) (Gros-Louis, F. et al. J. Biol. Chem. 279, 45951-45956 (2004)) and dynactin (DCTN1) (Puls, I. et al. Nature Genet. 33, 455-456 (2003)) are associated with ALS. Spastin27 and KIF5A (Reid, E. et al. Am. J. Hum. Genet. 71, 1189-1194 (2002)) are mutated in hereditary spastic paraplegia, whereas Charcot-Marie-Tooth neuropathy type 2E (Mersiyanova, I. V. et al. Am. J. Hum. Genet. 67, 37-46 (2000)) is caused by mutations in the neurofilament light polypeptide (NEFL) gene. Furthermore, several mouse models clearly document that defects in cytoskeletal proteins can cause motor neuron disease (Perrot, R. & Eyer, J. Brain Res. Bull. 80, 282-295 (2009)). Reported herein is that mutations in the PFN1 gene account for 1-2% of FALS. The observations herein emphasize that disruption of cytoskeletal pathways contribute importantly to ALS pathogenesis.

Methods Summary

Exome sequencing was accomplished using an exome array (SeqCap EZ Exome Library, Nimblegen) adapted for sequencing on the Illumina DNA sequencing platform. Alignment of sequence to the human genome and variant detection was accomplished using the applications SOAPaligner and SOAPsnp. Expression constructs for wild-type and mutant PFN1 were transfected into N2A cells using Lipofectamine 2000 (Invitrogen). Inhibition of proteasome activity in N2A cells was performed by incubation with 10 μM MG132 (Sigma-Aldrich) after transfection for 16 h before collection. Insolubility of PFN1 mutants was assessed by sequential NP-40/urea protein extraction followed by western blot analysis. Transfected HEK293 cells were lysed at 24 h with RIPA buffer and immunoprecitated with an anti-V5 antibody to investigate the interactions of PFN1 and actin. Primary motor neurons were isolated and cultured from embryonic day (E)13.5 mouse embryos and transfected by magnetofection. Axon length measurements were determined from low magnification images (×10). The length of the longest axon branch was measured using ImageJ plug-in Neuron J. F-actin and G-actin were labelled with fluorescent-conjugated Phalloidin (Invitrogen) and DNase I (Invitrogen), respectively. Deconvolution of images was performed using Autoquant (MediaCybernetics). The growth cone area and the fluorescence intensity for F-actin and G-actin staining were measured using ImageJ software.

Methods

Human Subjects

DNA samples were collected from familial and sporadic ALS cases and control individuals after informed consent was obtained. All protocols were approved by the Institutional Review Boards at the institutions involved. All familial ALS samples were prescreened for common mutations/expansions in SOD1, FUS, TARDBP, C9orf72, VCP, VAPB and ANG. A subset of the samples was obtained from the NINDS Repository at Coriell Cell Repositories.

Plasmids and Cloning

Figure 18:
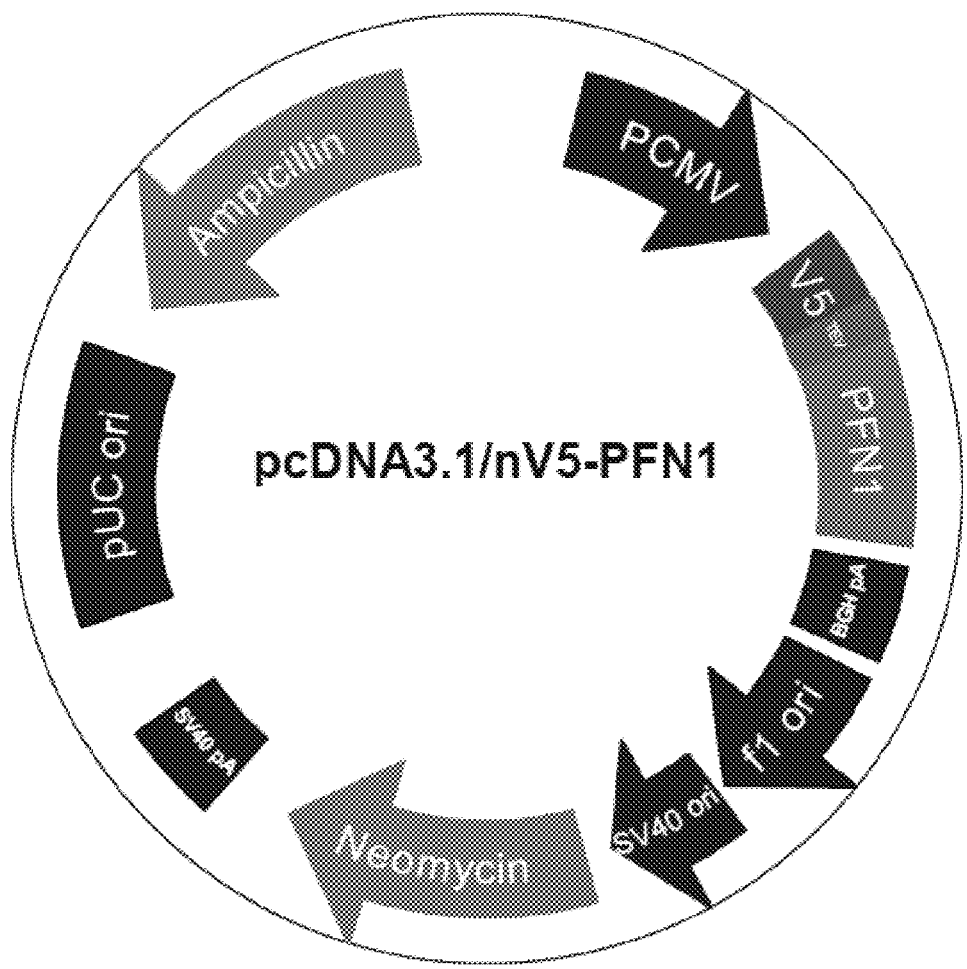
FIG. 18: Plasmid map of the V5-PFN1 expression constructs. The PFN1 gene was subcloned into the expression vector pcDNA3.1/nV5, as described in the exemplification. A map of the resultant construct is shown.

PFN1 expression vectors with V5 epitope tags were constructed using the backbone pcDNA3.1/nV5-DEST™ (Invitrogen) by way of Gateway® Technology according to manufacturer's protocol. In brief, attB-flanked primers were used to amplify PFN1 from human complementary DNA samples (Table 9). The PCR product was recombined into pDONR™ 221 to create the entry clone. pDONR221-PFN1 was then recombined with pcDNA3.1/nV5-DEST™ (Invitrogen) to create the wild-type PFN1 expression vector. For establishment of mutant PFN1 plasmids, site-directed mutagenesis was performed according to manufacturer's protocol Quickchange® Multi Site-Directed Mutagenesis Kit (Agilent). All constructs were verified by DNA sequencing. A plasmid map is shown in FIG. 18.

Linkage Analysis and Exome Sequencing

Linkage peaks were identified by subjecting DNA to genome-wide genotyping using the Affymetrix 10K SNP arrays and analysed using the software application Allegro v.2.0 (Gudbjartsson, D. F. et al. Nature Genet. 25, 12-13 (2000)) to generate multi-point lod scores. Only affected members (and married-in samples) were used for the analysis. Targeted exome capture and deep sequencing was accomplished using an exome array (SeqCap EZ Exome Library, Nimblegen) adapted for sequencing on the Illumina DNA sequencing platform (Choi, M. et al. Proc. Natl. Acad. Sci. USA 106, 19096-19101 (2009)). Paired-end sequencing was performed on either an IlluminaGenomeAnalyzer II or HiSeq2000. Alignment to the human genome (hg19) was accomplished using SOAPaligner (Li, R. et al. Bioinformatics 25, 1966-1967 (2009)) and quality control assessments were performed using SOAPcoverage. Variants were detected in each sample with the application SOAPsnp (Li, R. et al. Genome Res. 19, 1124-1132 (2009)) using the default settings. A minimum quality score of 10 was required to define a variant. The conversion of variants to amino acid position was accomplished using the software application SIFT (Kumar, P. et al. Nature Protocols 4, 1073-1081 (2009)) based on Ensembl annotation release 55. Filtering of variants was accomplished with a custom designed database using data from the 1000 Genomes Project (May 2011 release) (The 1000 Genomes Project Consortium. Nature 467, 1061-1073 (2010)) and the NHLBI ESP Exome Variant Server (5,379 sequenced exomes; evs.gs.washington.edu/EVS/).

Mutation Screening

Repeat expansion PCR for the hexanucleotide repeat expansion in the C9orf72 gene was performed as previously described (DeJesus-Hernandez, M. et al. Neuron 72, 245-256 (2011)). Sequencing of PFN1, PFN2, PFN3 and intron 2 of PFN1 was performed by touchdown PCR (30 cycles with annealing temperature starting at 65° C. and decreasing 0.5 uC per cycle, followed by 15 cycles with an annealing temperature of 65° C.), using primers with M13 tails (Table 9). Amplification was performed using either AmpliTaq Gold® (Applied Biosystems) or AccuPrime™ GC rich Polymerase (Invitrogen). DNA samples were extracted from either lymphoblastoid cell lines or whole blood; a subset of the samples was whole genome amplified using the GenomiPhi™ DNA amplification kit (GE Healthcare Lifesciences). PCR products were subsequently purified by incubation with exonuclease I and shrimp alkaline phosphatase, and sequenced at the Massachusetts General Hospital DNA Core Facility). Sequence analysis was performed using the PHRED/PHRAP/Consed software suite (www.phrap.org/) and variations in the sequences were identified with the Polyphred v6.15 software www.droog.gs.washington.edu/polyphred/). The sequencing primers are listed in Table 9.

Cell Culture and Transfections of N2A Cells

N2A cells were maintained in MEM with 10% fetal bovine serum, 2 mM L-glutamine and 100 U penicillin per 100 µg streptomycin at 5% $CO_2$. For cell lysis and western blot analyses, transfections were performed in 6-well plates with 4 µg of plasmid DNA using Lipofectamine™ 2000 (Invitrogen) according to the manufacturer's protocol. For immunofluorescence, cells were plated onto 12-mm round coverslips in 24-well plates and transfected with 0.8 mg of DNA.

Immunofluorescence of N2A Cells

Immunofluorescence was performed as previously described (Bosco, D. A. et al. Nature Neurosci. 13, 1396-1403 (2010)). In brief, at 48 h after transfection, cells were fixed with 4% paraformaldehyde at room temperature for 15 min, permeabilized with 1% Triton X-100 at room temperature for 10 min, and then blocked with blocking buffer (50 mM $NH_4Cl$, 10 mg $ml^{-1}$ BSA, 2% natural goat serum, 0.1% Triton X-100 in Dulbecco's PBS) at 37° C. for 1 h. Appropriate fluorophore-conjugated antibody was diluted in dilution buffer (0.1% Triton X-100, 0.15% goat serum in Dulbecco's PBS) and added at 4° C. overnight. After three washes with PBST (0.1% Tween-20), cells were mounted with Vectashield Hard Set™ Mounting Medium containing DAPI (Vector Laboratories). Confocal images were obtained with a 3100 Plan Apo oil objective lens on a Nikon TE-2000E2 inverted microscope (Nikon Instruments) with a Yokogawa CSU10 Spinning Disk Confocal Scan Head (Solamere Technology Group) and processed with ImageJ software. For confocal imaging, mouse Dylight 549-V5 antibody (1:100, AbDserotec) and rabbit Dylight 488-ubiquitin antibody (1:100, Enzo Life Sciences) were used. For aggregate counting, mouse Alexa Fluor® 488-V5 antibody (1:100, AbDserotec) was used. To count the number of cells containing insoluble aggregates, images were obtained with a Zeiss Axioskop 2 microscope with a 3100 objective. The images were processed with MetaMorph (v.7.5, Molecular Devices) image analysis software.

Fractionation of Insoluble/Soluble PFN1 and Western Blotting

Transfected cells were washed with cold PBS and then scraped directly in NP-40 lysis buffer (1% NP-40, 20 mM Tris-HCl, pH 7.4, 150 mM NaCl, 5 mM EDTA, 10% glycerol, 1 mM dithiothreitol (DTT), 10 mM sodium fluoride, 1 mM sodium orthovanadate and 5 mM sodium pyrophosphate) with EDTA-free protease inhibitors (Roche). The lysates were rotated for 30 min at 4° C. followed by centrifugation at 15,800 g for 20 min. The supernatant was removed and used as the soluble fraction. To remove carryovers, the pellet was washed with lysis buffer, and then resuspended in urea-SDS buffer (NP-40 lysis buffer with 8M urea, 3% SDS) followed by sonication. The lysate was then spun again for 20 min at 4° C. and the supernatant was removed (insoluble fraction). Protein concentrations were determined by the BCA assay. Western blot detection was performed on Odyssey® Infrared Imager (Li-Cor Biosciences). Antibodies for western blotting are as follows: mouse monoclonal anti-GAPDH (1:1,000, Sigma-Aldrich); mouse monoclonal anti-V5 (1:2,000, Invitrogen); polyclonal IRDye 800CW goat anti-mouse IgG (1:8,000, LI-COR); polyclonal IRDye 680 goat anti-rabbit IgG (1:8,000, LI-COR); and polyclonal IRDye 800CW goat anti-rabbit IgG (1:8,000, LI-COR). To inhibit proteasome activity in N2A cells, cells were incubated with 10 mM MG132 (Sigma-Aldrich) after transfection for 16 h before collection.

Immunoprecipitations

V5-PFN1-transfected HEK293 cells were lysed at 24 h with RIPA buffer (150 mM NaCl, 50 mM Tris-HCl, pH7.5, 1% NP40, 0.1% SDS, 0.5% sodium deoxycholate, 5 mM EDTA, 10 mM sodium fluoride, 1 mM sodium orthovanadate and 1× protease inhibitor cocktail). The lysates were precleared with Dynabeads® Protein G (Invitrogen) followed by immunoprecipitation with 1 mg anti-V5 antibody at 4° C. overnight followed by incubation with Dynabeads® Protein G for 1 h. The protein-bead complexes were washed four times with RIPA buffer, eluted by boiling at 95° C. for 5 min and then subjected to western blot analysis to detect V5-PFN1 and actin. Antibodies: mouse anti-V5 (1:5,000, Invitrogen); mouse anti-β-actin (1:1,000, Sigma); and goat anti-mouse 800CW (1:10,000, LICOR). To demonstrate conjugation of mutant PFN1 by ubiquitin, HA-ubiquitin was co-transfected into N2A with either V5-PFN1 (C71G) or V5 vector at a ratio of 1:1. At 48 h after transfection, cells were lysed and soluble fractions were prepared as described above. NP-40-resistant pellets were further dissolved in RIPA buffer and immunoprecipitated with 1 mg anti-V5 antibody and washed with lysis buffer three times. Western blot analysis was performed with an anti-HA-biotin antibody (1:2,000, sigma) and IRDye® 800CW streptavidin (1:2,000, LI-COR). After stripping the membrane, it was reprobed with mouse anti-V5 antibody (1:5,000, Invitrogen).

Primary Motor Neuron Culture, Transfection and Immunofluorescence

Figure 19:
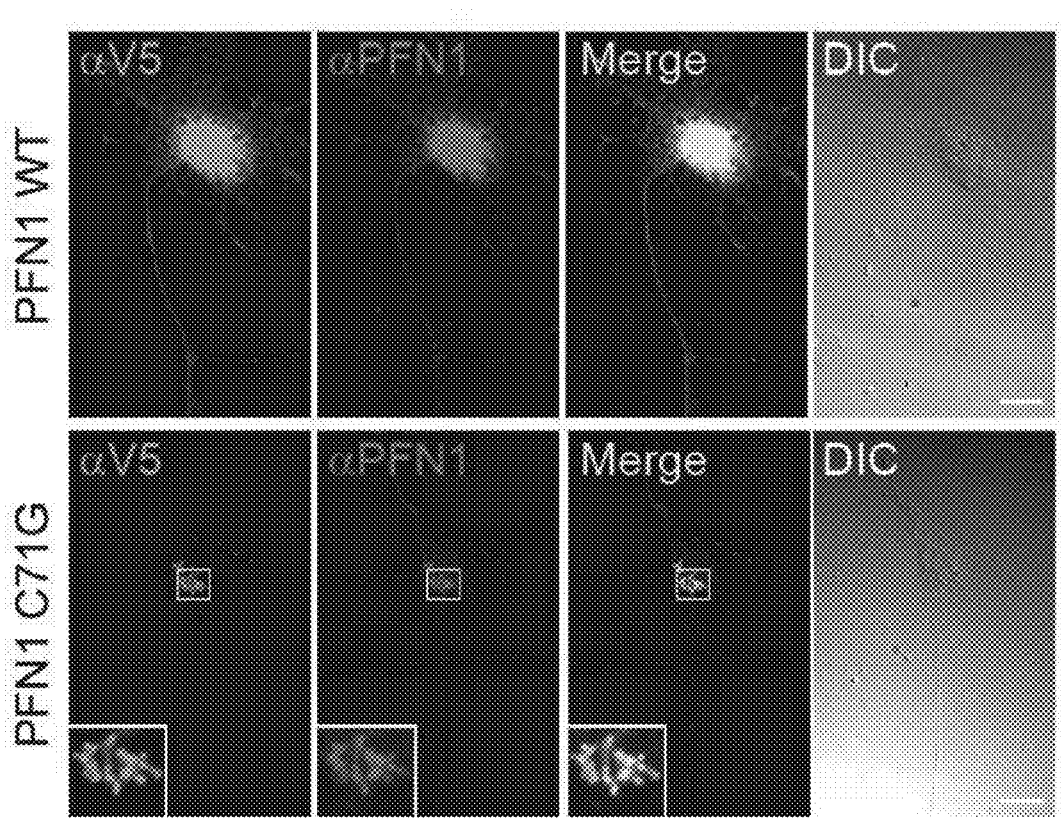
FIG. 19: V5 antibodies recognize the V5-PFN1 expressed protein. Primary motor neurons were transfected with constructs expressing V5-PFN1. At twenty-four hours post transfection, the cells were fixed and stained with anti-V5 and anti-PFN1 antibodies. Co-localization of the staining confirms that the V5 antibody recognizes the V5-PFN1 expressed protein. Scale: 100 µm.

Primary motor neurons from embryonic day (E)13.5 mouse embryos were isolated, cultured and transfected as previously described (Fallini, C. et al. Mol. Neurodegener. 5, 17 (2010)). Ubiquitin protein fused to an HA tag was cloned into the pcDNAplasmid by PCR amplification. To inhibit proteasome activity, cells were treated with 10 mM G132 for 12 h. Motor neurons were fixed for 15 min with 4% paraformaldehyde in PBS two or three days after transfection, as indicated. Anti-V5 (1:1,000; Invitrogen), HA (1:1,000; Cell Signaling Technology), TDP-43 (1:500, ProteinTech Group), FUS (1:500, Bethyl labs), SMN (1:500, Santa Cruz) and PFN1 (1:500, Sigma) antibodies were incubated overnight at 4° C. Dylight488-, Cy3-, Cy2- or Cy5-conjugated secondary antibodies (Jackson Immunoresearch) were incubated for 1 h at room temperature. Cell staining with anti-PFN1 and anti-V5 yielded overlapping staining patterns (FIG. 19). F-actin and G-actin were labelled with rhodamine-conjugated phalloidin (1:1,000, Invitrogen) and Alexa488-DNase I (1:250, Invitrogen), respectively. Z-series (5-10 sections, 0.2 mm thickness) were acquired with an epifluorescence microscope (Ti, Nikon) equipped with a cooled CCD camera (HQ2, Photometrics). Images were deconvolved (Autoquant, MediaCybernetics) and analysed. The growth cone area and the fluorescence intensity for F-actin and G-actin staining was measured using ImageJ software. The ratio between the two values was averaged and compared between different conditions. Statistical significance was assessed using Kruskas-Wallis one-way ANOVA test and Dunn's post-hoc test. For the analysis of axon length, cells were fixed and stained to detect V5-PFN1 at 3 days after transfection. Low magnification images (×10) were acquired and, if necessary, reassembled in Adobe Photoshop. The axon was identified morphologically as the longest neurite. The length of the longest axon branch was measured using ImageJ plug-in NeuronJ (Meijering, E. et al. Cytometry A 58A, 167-176 (2004)). Statistical significance was assessed with the Kolmogorov-Smirnov test.

Immunohistochemistry

Paraffin-embedded sections from post-mortem human spinal cord (8 mm thick) were deparaffinized and endogenous peroxidase activity was blocked with 3% hydrogen peroxide at 40° C. Sections were then incubated with normal horse serum for 15 min at 40° C., followed by anti-PFN1 primary antibody (1:2,000, Sigma rabbit polyclonal) or anti-pTDP-43 (1:8,000, Cosmo Bio) diluted in 1% BSA overnight at 4° C. The next day, sections were incubated with biotinylated secondary antibody for 30 min at 37° C. followed by avidin-biotin peroxidase complex (Vector Laboratories) for 60 min at 37° C. DAB (3,39-diaminobenzidine) was used as the chromogen (for colour development); tissues were then counterstained with haematoxylin.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of identifying an individual that has amyotrophic lateral sclerosis (ALS), or is at risk of developing ALS, comprising:
   a) selectively sequencing a profilin 1 (PFN1) gene sequence in a sample of an individual in need thereof; and
   b) detecting one or more alterations in the PFN1 gene sequence of the individual compared to a wild type PFN1 gene sequence, wherein the one or more alterations results in the PFN1 gene sequence encoding a PFN1 protein having a C71G alteration, a M114T alteration, a G118V alteration, an E117G alteration or a combination thereof, wherein if the one or more alterations are detected then the individual has ALS.

2. The method of claim 1 wherein the ALS is familial amyotrophic lateral sclerosis (FALS).

3. The method of claim 1 wherein the method further comprises obtaining a sample from the individual.

4. The method of claim 3 wherein the sample is obtained from a biological fluid of the individual, a biological tissue of the individual or a combination thereof.

5. The method of claim 1 wherein the one or more alterations in the PFN1 sequence is detected using exome sequencing, sanger gene sequencing, resequencing array analysis, mRNA analysis/cDNA sequencing polymerase chain reaction (PCR), single-strand conformation polymorphism (sscp), heteroduplex analysis (het), allele-specific oligonucleotide (aso), restriction fragment analysis, allele-specific amplification (asa), single nucleotide primer extension, oligonucleotide ligation assay (ola), denaturing gradient gel electrophoresis (DGGE), temperature gradient gel electrophoresis (TGGE) and single strand conformation polymorphism (SSCP), or combinations thereof.

6. The method of claim 5 wherein the one or more alterations in the PFN1 sequence is detected using exome sequencing.

7. The method of claim 1 wherein the detection of the one or more alterations in the PFN1 sequence of the individual is compared to a control.

8. The method of claim 7 wherein the control is a wild type PFN1 gene sequence.

9. The method of claim 7 wherein the control is a PFN1 gene sequence sample obtained from one or more individuals that do not have ALS or FALS.

10. The method of claim 1 wherein the individual is a human.

11. The method of claim 1 wherein the individual is symptomatic for ALS or FALS.

12. The method of claim 1 wherein the individual is asymptomatic for ALS or FALS.

13. The method of claim 2 wherein the individual has been previously diagnosed with ALS.

14. The method of claim 1 further comprising treating the individual for ALS or FALS.

* * * * *